United States Patent [19]
Grdina

[11] Patent Number: 5,869,338
[45] Date of Patent: Feb. 9, 1999

[54] METHOD FOR PROTECTION AGAINST GENOTOXIC MUTAGENESIS

[75] Inventor: David J. Grdina, Naperville, Ill.

[73] Assignee: Arch Development Corporation, Chicago, Ill.

[21] Appl. No.: 481,885

[22] Filed: Jun. 7, 1995

Related U.S. Application Data

[63] Continuation-in-part of Ser. No. 121,946, Sep. 13, 1993, Pat. No. 5,567,686, which is a continuation-in-part of Ser. No. 851,210, Mar. 13, 1992, Pat. No. 5,488,042.

[51] Int. Cl.$^6$ .............................. C12N 5/06; A61K 31/70; A61K 31/13; A61K 31/685
[52] U.S. Cl. .............................. 435/375; 514/43; 514/76; 514/269; 514/299; 514/546; 514/663; 514/917
[58] Field of Search .............................. 424/10; 514/299, 514/269, 917, 76, 546, 663, 43; 435/172.1, 375

[56] References Cited

U.S. PATENT DOCUMENTS

| | | | |
|---|---|---|---|
| 5,292,497 | 3/1994 | Schein et al. | 424/10 |
| 5,298,499 | 3/1994 | Carroll et al. | 514/114 |
| 5,434,145 | 7/1995 | Edwards et al. | 514/108 |
| 5,488,042 | 1/1996 | Grdina | 514/114 |
| 5,567,686 | 10/1996 | Grdina | 514/43 |

FOREIGN PATENT DOCUMENTS

| | | |
|---|---|---|
| WO 89/05637 | 6/1989 | WIPO . |
| WO 90/14007 | 11/1990 | WIPO . |

OTHER PUBLICATIONS

"Abstracts," 3$^{rd}$ International Conference on Anticarcinogenesis & Radiation Protection, Oct. 15–21, 1989.
"Abstracts," Twenty–eighth Plenary Meeting of the Committee on Space Research, Jun. 26–Jul. 6, 1990.
Applegate, L.A., Lautler, D. and Tyrrell, R.M., "Endogenous Glutathoine Levels Modulate the Frequency of Both Spontaneous and Long Wavelength Ultraviolet Induced Mutations in Human Cells," *Carcinogenesis*, 13(9):1557–1560, 1992.
Benova, D., "Antimutagenic Properties of WR 2721 and of a Radioprotective Mixture, ATP–AET–Serotonin, With Regard to X Ray Induced Reciprocal Translocations in Mouse Spermatogonia," *Int. J. Radiation Oncology Biol. Phys.*, 13, 117–119, 1987.
Brown, J.M., Sensitizers and Protectors and Radiotherapy, *Cancer*, 2222–22228, May 1 Supplement, 1985.
Carnes, B.A. and Grdina, D.J., "In Vivo protection by the Aminothiol WR–2721 Against Neutron–Induced Carcinogenesis," *Int. J. Radiat. Biol.*, 61, 567–576, 1992. (Supported in part by the U.S. Department of Energy, Office of Health and Environment Research, under contract W–31–109–ENG–38, the Center of Radiation Therapy and NIH–NCI grant CA–37435.).

Constine, L.S., Zagars, G., Rubin, P., and Kligerman, M., "Protection by WR–2721 of Human Bone Marrow Function Following Irradiation," *Int. J. Radiation Oncology Biol. Phys.*, 12:1505–1508, 1986.
Corn, B.W., Liber, H.L., and Little, J.B., "Differential Effects of Radical Scavengers on X–Ray–Induced Mutation and Cytotoxicity in Human Cells," *Radiation Research*, 109:100–108, 1987.
Fry, R.J.M., "Radiation Carcinogenesis: Radioprotectors and Photosensitizers," *Radioprotectors and Anticarcinogens*, 417–436, 1983. (Supported by the Office of Health and Environmental Research, U.S. Department of Energy, under contract W–7405–eng–26 with the Union Carbide Corporation).
Grdina, D.J., P. Dale, and R. Weichselbaum. Protection Against AZT–Induced Mutagenesis at the HGPRT Locus in a Human Cell Line by WR–151326. *International Journal of Radiation Oncology, Biology, Physics*, 22:813–815, 1992. Presented at the Seventh International Conference on Chemical Modifiers for Cancer Treatment, Clearwater, Florida, Feb. 2–5, 1991. (Supported in part by the U.S. Department of Energy, Office of Health and Environmental Research, under contract W–31–109–ENG–38;NIH/NCI grant CA–37435, U.S. Bioscience Inc. and the Center for Radiation Therapy.).
Grdina, D.J., B.A. Carnes, D. Grahn, and C.P. Sigdestad. Protection Against Late Effects of Radation by S–2–(3–Aminopropylamino)–Ethylphosphorothioic Acid. *Cancer Research*, 51:4125–4130, 1991. (Supported by the U.S. Department of Energy, under contract W–31–109–ENG–38; by NIH/NCI grant CA–37435 and by the center for Radiation Therapy.).
Grdina, D.J., B. Nagy, C.K. Hill, and C.P. Sigdestad. Protection Against Radiation–Induced Mutagenesis in V79 Cells by 2–[(Aminopropyl)amino] Ethanethiol Under Conditions of Acute Hypoxia. *Radiation Research*, 117:251–258, 1989.
Grdina, D.J. and C.P. Sigdestad. Radiation Protectors: The Unexpected Benefits. *Drug Metabolism Reviews*, 20(1):13 42, 198. (Supported in part by the U.S. Department of Energy, Office of Health and Environmental Research under contract W–31–103–ENG–38 and Public Health Service grant CA37435 awareded (D.J.G.) by the National Cancer Institute, Department of Human Services; and the U.S. Army Medical Research and Development Command, Fort Detrick, Maryland, under contracts DAMD17–86–C–6229 and DAMD17–C–7218 (C.P.S.).).
Grdina and Sigdestad, "Exhibit 1," (FIG. 1–Radiation Inactivation of Mammalian Cells).

(List continued on next page.)

*Primary Examiner*—Nancy Degen
*Attorney, Agent, or Firm*—Arnold, White & Durkee

[57] ABSTRACT

A method and pharmaceutical for protecting against mutational damage in mammalian cells, irrespective of the nature of the mutagenic event or source of radiational or chemical insult or the like.

45 Claims, 40 Drawing Sheets

OTHER PUBLICATIONS

Grdina, D.J., Y. Kataoka, I. Basic, and J. Perrin. The Radioprotector WR–2721 Reduces Neutron–Induced Mutations at the Hypoxanthine–Guanine Phosphoribosyl Transferase Locus in Mouse Splenocytes When Administered Prior to or Following Irradiation. *Carcinogenesis,* vol. 13, No. 5, pp. 811–814, 1992. (Supported in part by the U.S. Department of Energy, Office of Health and Environmental Research, under contract W–31–109–ENG–38; NIH/NCI CA–37435 and the Center for Radiation Therapy in Chicago, Illinois.).

Grdina, D.J., B.J. Wright, and B.A. Carnes. Protection by WR–151327 Against Late Effects Damage Induced by Fission–Spectrum Neutrons. *Radiation Research,* 128(S):124–127, 1991. (Supported in part by the U.S. Department of Energy, Office of Health and Environmental Research, under contract W–31–109–ENG–38; Center for Radiation Therapy and NIH–NCI grant CA–37435.).

Grdina, D.J., B. Nagy, C.K. Hill, R.L. Wells, and C. Peraino. The Radioprotector WR1065 Reduces Radiation–Induced Mutations at the HGPRT Locus in V79 Cells. *Carcinogenesis,* 6(6):929 931, 1985.

Grdina, D.J. and Meechan, P.J., "Effects of the Radioprotector WR–1065 on Normal Human Skin Fibroblast Cells in Culture," Radiation Research Meeting, Mar. 19–25, 1993.

Grdina, D.J., Constantinou, A., and Shigematsu, N., "Inhibition of Topoisomerase II Activity in Repair–Proficient CHO K1 Cells by WR–1065," Radiation Research Meeting, Mar. 19–25, 1993.

Held, K.D., "Models for Thiol Protection of DNA in Cells," *Pharmac. Ther.,* 39:123–131, 1988. (Supported in part by PHS grants CA42167 awarded by the National Cancer Institute, DHHS).

Holmes, G.E., Bernstein, C., and Bernstein, H., "Oxidative and Other DNA Damages as the Basis of Aging: A Review," *Mutation Research,* 275:305–315, 1992.

Holwitt, E.A., oda, E, and Swenberg, C.E., "Enhancement of Topoisomerase I–Mediated Unwinding of Supercoiled DNA by the Radioprotector WR–33278," *Radiation Research,* 124:107–109, 1990.

Kataoka, Y., I. Basic J. Perrin, and D.J. Grdina. Anti–Mutagenic Effects of Radioprotector WR–2721 Against Fission–Spectrum Neutrons and $^{60}$Co –Rays in Mice, *International Journal of Radiation Biology,* #3, 61:387–392, 1992. (Supported in part by the U.S. Department of Energy, Office og Health and Environmental Research, under contract W–31–109–ENG–38; NIH/NCI CA–37435 and the Center for Radiation Therapy in Chicago, Illinois.).

Kataoka, Y., Shigematsu, N., O'Connor, T., Ward, W., and Grdina, D.J., "Captoril Protects Against Mutagenesis at the HPRT Locus in $^{60}$Co y–Ray–Irradiated CHO–AA8 Cells," *Radiation Research Meeting,* Mar. 19–25, 1993.

Kataoka, Y., Perrin, J., and Grdina, D.J., "Protection by WR2721 Against Fission–Neutron–Induced Mutagenesis in Mice".

Kirkwood, T.B.L., "DNA, Mutations, and Aging," *Mutation Research,* 219:1–7, 1989.

Linnane, A.W., Zhang, C., Baumer, A., and Nagley, P., "Mitochondrial DNA Mutation and the Ageing Process: Bioenergy and Pharmacological Intervention," *Mutation Research,* 275:195–208, 1992.

Livesy, *Biochemical Pharmacology,* 39 1807, 1990.

Mahoney, F., "Summary Statement," Radiation Study Section, Feb., 1986.

Maisin, J.R., Mattelin, G., and Lambiet–Collier, M., Chemical Protection Against the Long–Term Effects of a Single Whole–Body Exposure of Mice to Ionizing Radiation, *Radiation Research,* 71:119–131, 1977.

Milas, L., Hunter, N., and Stephens, L.C., and Peters, L.J., :Inhibition of Radiation Carcinogenesis in Mice by S–2(3–Aminopropylamino)–Methylphosphorothioic Acid, *Cancer Research,* 44:5567–5569, Dec. 1984. (Supported in part by grants CA–06294 and CA–16672, provided by the National Cancer Institute Department of of Health and Human Services).

Minnunni, M., Wolleb, U., Mueller, O., Pfeifer, A., Aeschbacher, H.U., "Natural Antioxidants as Inhibitors of Oxygen Species Induced Mutagenicity," *Mutation Research,* 269:193–200, 1992.

Nagy, B., and D.J. Grdina. Protective Effects of 2–[(Aminopropyl) Amino] Ethanethiol Against Bleomycin, Nitrogen Mustard, Cis–Diamminedichloroplatinum, and Radiation Induced Mutagenicity in V–79 Cells, *International Journal of Radiation Oncology, Biology, Physics,* 12:1475 1478, Aug., 1986

Nagy, B., P.J. Dale, and D.J. Grdina. Protection Against Cis–Diammine–dichloroplatinum (II) Cytotoxicity and Mutagenicity in V79 Cells by Free Radical Scavenger 2–[(aminopropyl)amino] Ethanethiol. *Cancer Research,* 46:1132 1135, Mar. 1986.

"1990 AACR Abstract Form" Temporary Abst. No. 247, of the paper Antimutagenic and Anticarcinogenic Effects of Aminothiols: Applications to the Clinic and Workplace. (Supported in part by U.S. Department of Energy contract W–31–109–ENG–38; NIH–NCI CA–37435 and the Center for Radiation Therapy in Chicago, Illinois).

Nygaard, O.F., and Simic, MG., excerpt from *Radioprotectors and Anticarcinogens,* 73–85, 1983.

"Preface: Ageing of the 25th Chromosome," *Mutation Research,* 275:113–114, 1992.

Rosin, M.P., and Stich, H.F., "The Inhibitory Effect of Cysteine on the Mutagenic Activities of Several Carconogens," Mutation Research, 54:73–81, 1978.

Smoluk, G.D., Fahey, R.C., Calabro–Jones, P.M., Aguilera, J.A., and Ward, J.F., "Radioprotection of Cells in Culture by Wr–2721 and Derivatives: Form the Drug Responsible for Protection," *Cancer Research,* 48:3641–3647, Jul. 1, 1988. (Supported by grant CA–39582 from the National Cancer Institute.).

"Summary Statement," Radiation Study Section, Jan., 1989.

Sweeney, R.T., "A Survey of Compounds from the Antiradiation Drug Development program of the U.S. Army Medical Research and Development Command," Walter Reed Army Institute of Research, Washington, D.C., Sep., 1979.

Van Beek, M.E.A.B., R.L. Doak, C.P., Sigdestad, and D.J. Grdina. Pathological Effects of the Radiation Protector WR151327 in Mice. *Radiation Research,* 124:79 84, 1990.

Wei, Y.H., "Mitochondrial DNA Alterations as Ageing–Associated Molecular Events," *Mutation Research,* 275:145–153, 1992.

Zhang, X., Lai, p., and Taylor, Y, "Differential Radioprotection of Cultured Human Diploud Fibroblasts and Fibrosarcoma Cells by Wr1065," *International Journal of Radiation Oncology, Biology, Physics,* 21, Supplemental 1, 1991.

Ando et al., "Radioprotection from Fast Neutron Irradiation by WR161327," *Inst. Phys. Chem. Res.,* 83:40–41, 1989.

Constantinou et al., "The Effect of Topoisomerase Inhibitors on the Expression of Differentiation Markers and Cell Cycle Progression in Human K–562 Leukemia Cells," *Experimental Cell Research,* 203:100–106, 1992.

Gordon et al., "Cellular Radiosensitivity in V79 Cells Is Linked to Alterations in Chromatin Structure," *Int. J. Radiation Oncology Biol. Phys.,* 19:1199–1201, 1990.

Gordon et al., "The Increase in Radioresistance of Chinese hamster Cells Cultured as Spheroids Is Correlated to Changes in Nuclear Morphology," *Radiation Research,* 121:175–179, 1990.

Grdina, et al., "Chemical Protection and Cell–Cycle Effects on Radiation–Induced Mutagenesis," *Cell Prolif.,* 25:23–29, 1991.

Grdina et al., "Effects of Radioproectors on DNA Damage and Repair, Proteins, and Cell–Cycle Progression," *Pharmac. Ther.,* 39:133–137, 1988.

Grdina et al., "The Effect of 2–[(Aminopropyl)Amino] Ethanethiol on Fission–Neutron–Induced DNA Damage and Repair," *Br. J. Cancer,* 59:17–21, 1989.

Grdina & Nagy, "The Effect of 2–[(Aminopropyl)Amino] Ethanethiol. (WR1065) on Radiation–Induced DNA Damage and Repair and Cell Progression in V79 Cells," *Br. J. Cancer,* 54:933–941, 1986.

Grdina et al., "Inhibition of Topoisomerase II Alpha Activity in CHO K1 Cells by 2–[(Aminopropyl) Amino] Ethanethiol (WR–1065)," *Radation Research,* 138:44–52, 1994.

Grdina et al., "Protection by WR–2721 and WR–15327 Against Late Effects of Gamma Rays and neutrons," *Adv. Space Res.,* 12(2–3):(2)257–(2)263, 1992.

Grdina et al., "Protection by WR1065 and WR161326 Against Fission–Neutron–Induced Mutations at the HGPRT Locus in V79 Cells," *Radiation Research,* 117:500–510, 1989.

Grdina et al., "Protective Effect of S–2–(3–Aminopropylamino)Ethylphosphorothioic Acid Against Induction of Altered Hepatocyte Foci in Rats Treated Once with γ–Radiation within One Day After Birh," *Cancer Research,* 45:5379–5381, 1985.

Grdina, et al., "Radioprotectors in Treatment Therapy to Reduce Risk in Secondary Tumor Induction," *Pharmac. Ther.,* 39:21–25, 1988.

Grdina, et al., "Thiol and disulfide Metabolites of the Radiation protector and Potential Chemopreventive Agent WR–2711 Are Linked to Both Its Anti–Cytotoxic and Anti–Mutagenic Mechanisms of Action," *Carcinogenesis,* 16(4):767–774, 1995.

Hallahan et al., "The Isoquinoline Sulfonamide H7 Attenuates Radiation–Mediated Protein Kinase C Activation and Delays the Onset of X–Ray–Induced G2 Arrest," *Int. J. Radiation Oncology Biol. Phys.,* 24:687–692, 1992.

Hanson and Grdina, "Radiation–induced DNA Single–Strand Breaks in the Intestinal Mucosal Cells of Mice Treated with the Radioprotectors WR–2721 or 16–16 Dimethyl Prostaglandin $E_2$," *Int. J. Radiat. Biol.,* 52(1):67–76, 1987.

Hill et al., "2–[(Aminopropyl)Amino]Ethanethiol (WR1065) Is Anti–Neoplastic and Anti–Mutagenic When Given During $^{60}$Co γ–Ray Irradiation," *Carcinogensis,* 7(4):665–668, 1986.

Kataoka et al., "Antimutagenic Effects of Amifostine: Clinical Implications," *Seminars in Oncology,* 23(4) Suppl. 8:53–57, 1996.

Kataoka et al., "Induction of HPRT Mutations in Mice following Exposure to Fission–Spectrum Neutrons or (superscript) 60Co Gamma Rays," *Radiation Research,* 136:289–292, 1993.

Matsushita et al., "Radioprotection by WR–151327 Against the Late Normal Tissue Damage in Mouse Hind Legs From Gamma Ray Raidation," *Int. J. Radiation Oncology Biol. Phys.,* 30(4):867–872, 1994.

Meechan et al., "Association of Wr–1065 with CHO AA8 Cells, Nuclei, and Nucleoids," *Radiation Research,* 125:152–157, 1991.

Meechan et al., "Reversion of Radiosensitivity in Azacytidine–Treated XRS5 Cells Does Not Result in Full Radioprotection by WR–1065," *Int. J. Radiation Oncology Biol. Phys.,* 23:999–1002, 1991.

Murley et al., "Accumulation of CHO Cells in $G_2$ Phase Following Exposure to Wr–1065," *Radiation Research,* 126:223–228, 1991.

Murley et al., "Effects of Growth Media on Cell Cycle Progression in CHO Cells Exposed to the Radioprotector WR–1065,"*Cell Prolif.,* 25:643–650, 1992.

Murley and Gdina, "The Effects of Cycloheximide and WR–1065 on Radiation–Induced Repair Processes: A Mechanism for Chemoprevention," *Carcinogenesis,* 16(11):2699–2705, 1995.

Quiet et al., Variation in Radiation Sensitivity During the Cell Cycle of Two Human Squamous Cell Carcinomas, *Int. J. Radiation Oncology Biol. Phys.,* 20:733–738, 1990.

Schwartz et al., "2–{(Aminopropyl)Amino} Ethanethiol–Mediated Reductions in $^{60}$Co γ–Ray and Fission–Spectrum Neutron–Induced Chromosome Damage in V79 Cells," *Radiation Research,* 113:145–154, 1988.

Shigematsu et al., "Protection Against Radiation–Induced Mutations at the hprt locus by sermine and N,N'–(dithiodi–2–1–Ethanediyl)bis–1,3–Propanediamine (WR–33278)," *Mutagenesis,* 9:355–360, 1994.

Sigdestad et al., "Cell Cycle Redistribution of Cultured Cells After Treatment with Chemical Radiation Protectors," *Cell Tissue Kinet.,* 21:193–200, 1988.

Sigdestad et al., "Chemical Radiation protection from Fission Spectrum Neutrons," *Nuclear Science Applications,* 4:157–166, 1991.

Sigdestad et al., "A Comparison of Radioprotection from Three Neutron Sources and $^{60}$Co by WR–2721 and Wr–151327," *Radiation Research,* 106:224–233, 1986.

Sigdestad et al., "The Effect of Chemical Radiation Protectors on Cell Cycle Progression After Gamma or Neutron Irradiation," *Cell Prolif.,* 24:271–280, 1991.

Sigdestad et al., "The Effect of 2–[(Aminopropyl)Amino] Ethanethiol (WR–1065) on Radiation Induced DNA Double Strand Damage and Repair in V79 Cells," *Br. J. Cancer,* 55:477–482, 1987.

Vaughan et al. "Conformational Chnges in Chromatin Structure Induced by the Radioprotective Amonothiol, WR 1065," *Br. J. Cancer,* 60:893–896, 1989.

Woloschak et al., "Expression of Thymidine Kinase RNA and a Related Transcript is Modulated by Radioprotector WR–1065," *Cancer Research,* 55:4788–4792, 1995.

Orkin et al. Report & Recommendations of the Panel to Assess the NIH Investment In Research on Gene Therapy, 1995.

Shaw et al. Human Pharmacokinetics of WR–2721 Int J. Radiation Oncol Biol Phys. 12: 1501–1508, 1986.

Gyzewska, Teratogenesis, Caprinogenesis and Mutagenesis 15 (3) 109–14 (1995).

Gridna et al, Carcinogenesis 16(4), 767–74 (1995).

Glick, Int. J. Radiaton, Oncology, Biology, Physics. 10 (9) 1777–80 1984.

WR-33278

SPERMINE

3-[(2-MERCAPTOETHYL) AMINO] PROPIONAMIDE P-TOLUENESULFONATE  (WR-2529)

$$H_2NCCH_2\ NH\ CH_2\ CH_2\text{-}SH\text{-}(CH_3\text{-}\emptyset\text{-}SO_3H)$$
with O double-bonded to the first C

FIG. 7A

S-1-(2-HYDROXY-3-AMINO) PROPYL PHOSPHOROTHIOIC ACID  (WR-77913)

$$H_2N\ CH_2\ CH\ (OH)\ CH_2\ SPO_3\ H_2$$

FIG. 7B

2-[3-(METHYLAMINO) PROPYLAMINO] ETHANETHIOL  (WR-255591)

S-1-(AMINOETHYL) PHOSPHOROTHIOIC ACID  (WR-638)

$$H_2N\ CH_2\ CH_2\ SPO_3\ H_2$$

FIG. 7D

S-[2-(3-METHYLAMINOPROPYL) AMINOETHYL] PHOSPHOROTHIOATE ACID  (WR-3689)

$$CH_3NH\ (CH_2)_3\ NHCH_2\ CH_2\ SPO_3\ H_2$$

FIG. 7E

S-2-(4-AMINOBUTYLAMINO) ETHYLPHOSPHOROTHIOIC ACID  (WR-2822)

$$H_2N\ (CH_2)_4\ NH\ CH_2\ CH_2\ CH_2\ SPO_3\ H_2$$

FIG. 7F

S-2-(5-AMINOPENTYLAMINO) ETHYL PHOSPHOROTHIOIC ACID  (WR-2823)

$H_2N\ (CH_2)_5\ NH\ CH_2\ CH_2\ SPO_3\ H_2$

1-[3-(3-AMINOPROPYL) THIAZOLIDIN-2-YL]-D-GLUCO-1,2,3,4,5-  (WR-255709)
PENTANE-PENTOL DEHYDROCHLORIDE

S-2-(3-AMINOPROPYLAMINO) ETHYLPHOSPHOROTHIOIC ACID  (WR-2721)

$NH_2(CH_2)_3\ NH\ CH_2\ CH_2\ S\ PO_3\ H_2$

2-[(AMINOPROPYL) AMINO] ETHANETHIOL  (WR-1065)

$NH_2(CH_2)_3\ NH\ CH_2\ CH_2\ SH$

| CELL TYPE | WR-1065 | γ-RAY | TOPO I (UNITS/μg PROTEIN) | TOPO IIα |
|---|---|---|---|---|
| K1 | — | — | 112 ± 20 | 59 ± 14 |
| K1 | + | — | 97 ± 28 | 26 ± 3 |
| K1 | — | + | 82 ± 22 | 53 ± 28 |
| K1 | + | + | 96 ± 28 | 36 ± 13 |

FIG. 10A

| CELL TYPE | WR-1065 | γ-RAY | 100 X AREA |
|---|---|---|---|
| K1 | — | — | 167 ± 55 |
| K1 | + | — | 179 ± 49 |
| K1 | — | + | 219 ± 21 |
| K1 | + | + | 163 ± 39 |

FIG. 10B

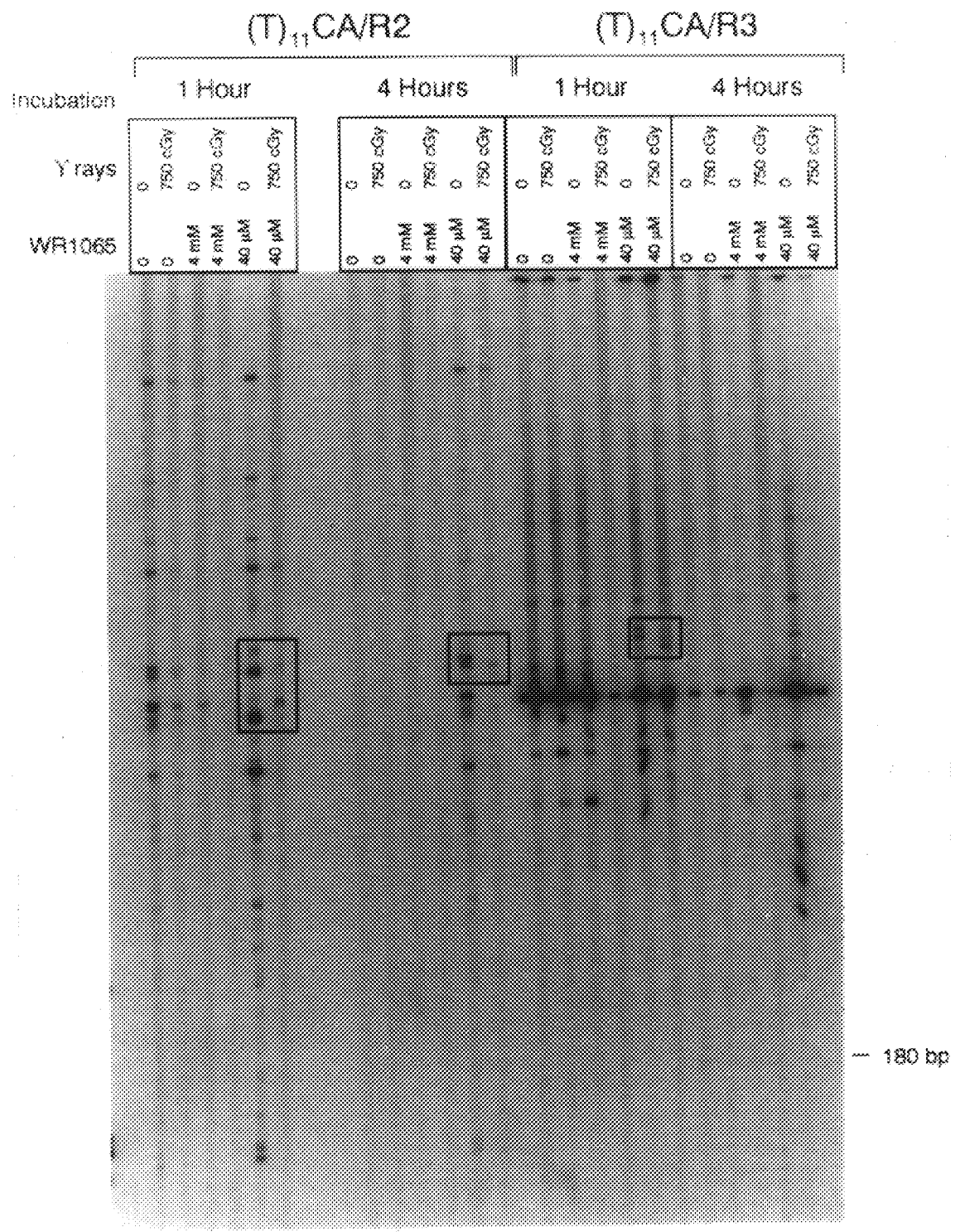
FIG. 18  Differential Display WR1065 γ Rays

```
       Q  :  ACT..CT.GGATGGGTTGGGGT..CGGGNTGAACAGGTNA
  H (1031) :  ACTCCCTCTCC....TTGGGGTG.AGGG....ACA.....
  M  (880) :  TCTTCCT....TG..TTGG..TGGCTGG.TTTTCA.GT..
  CHO (987):  TCTTCCT.TC.....TTGG..TGGCT.....TCCA.GT..

Q: CCTG.....CCCCTTNG.TGTNAAG.CAATGAGN......
          H: ......GAGCCCCAC.GCTGTT..GAC.ATCAGCCT....
          M: .CTGA.GAGCCCCAC.CCT..CAC...CAA...GGCTCCAG
        CHO: .CTCAAGGGCCCCGCCCC...CA.G.CAA.........G

Q: ...........ATCCCCCNCAANCAACACCTGTCAA...C
          H: GCTTCT......TCCCC...........TCTGCGGCTTTC
          M: GCCTCTCACAGCTCCCCC................ATTTA
        CHO: GCTT..............CA...CAAC.CC..TCACTTT.

Q: ACCTGTC..AA.....CTNATAA.TGNCAT.TGTCTAGCNC
          H: AC.TG.CTGAG..TTTCT.GTTC.TC..CC.TGGGAAG...
          M: ...TGCCTAAACATTCT..CTCCTC.A......GAA....
        CHO: ..GTG.CTGAAG...CTTG.ACC.C.ACAATGGC...C..

Q: AACCTGTGCTC........CCTCGTNG...ATTGGTG.
          H: ..CCTGTGC...CAGC.A.CCT..TTG...A.....GC
          M: ..CCTGTGCTCTTAGTGAGCC.ATTTTC...TT.GTGC
        CHO: ..CCT.AGC....GGTGT..CT..TTACAAAGTGGTGC

Q: TGT...AA......N.A.AATN.GNCT..GGA.T..GTG
          H: ....CT..TGGCCC.ACACTGAGGCTTAGGCCTCTCTG
          M: ....AAAATGG....ACAAT....ATTAAA.....GT.
        CHO: TGTTCT..TG.CCCTACTCAGAGCCCCAAGACTCAG.G
```

FIG. 19

|  | No. of Fibrosarcoma Lung Colonies | HPRT Mutant Frequency |
|---|---|---|
| UNTREATED | 68±10 (S.E.M.) | $15 \times 10^{-5}$ |
| CYTOXAN ONLY (100 mg/kg) | 0.5±0.3 | $160 \times 10^{-5}$ |
| WR-2721 ONLY (100 mg/kg) | 61.3±8.9 | $15 \times 10^{-5}$ |
| WR-2721 Administered 30 min Before Cytoxan | 0.5±0.3 | $35 \times 10^{-5}$ |
| WR-2721 Administered 2 hr After Cytoxan | 0.9±0.3 | $28 \times 10^{-5}$ |

FIG. 21

METHOD FOR PROTECTION AGAINST GENOTOXIC MUTAGENESIS

This is a continuation-in-part of application Ser. No. 08/121,946 filed on Sep. 13, 1993; now U.S. Pat. No. 5,567,686, which is a continuation in part of application Ser. No. 07/851,210 filed Mar. 13, 1992 on now U.S. Pat. No. 5,488,042.

This invention was made with Government support under Contract No. W-31-109-ENG-38 between the University of Chicago and the U.S. Department of Energy. The Government has certain rights in this invention.

The present invention is generally directed to a method for protecting against genomic destabilization in mammalian cells from chemical or radiational mutagenic events and the like. More particularly, the invention is concerned with mutation reduction through use of S-ω(ω-aminoalkylamino) alkyl dihydrogen phosphorothioates and their corresponding metabolites.

Classic somatic mutation models of aging hold that the aging function is the result of an accumulation, over time, of mutational events in nuclear DNA; see, Kirkwood, *Mutat. Res.*, Vol. 219, pp. 1–7 (1988), and/or mitochondrial DNA (mtDNA); see Linnane, et al, *Mutat. Res.* Vol. 275, pp. 195–208 (1992). With respect to the contribution of mtDNA mutations to the phenotype of aging, the central premise is that accumulation of random mutations in the cellular population is a major contributor to the gradual loss of cellular bioenergy capacity within tissues and organs, and that general senescence and diseases of aging are associated therewith.

Deletions of mtDNA were previously thought to occur only in individuals with neuromuscular disease. However, one particular deletion (mtDNA$^{4977}$) accumulates with age primarily in non-dividing muscle and brain cells. Consistent with the contribution of mtDNA to aging is that the genome of this organelle appears especially sensitive to endogenous and environmental mutagens, given the lack of protective histones. It is postulated that deleted mtDNA and DNA fragments may be further degraded or translocated from the mitochondria to the nucleus, a route substantiated by observations of inserted mtDNA sequences into nuclear DNA. Thus, it is speculated that fragments of migrating mtDNA may change the information content and expression of certain nuclear genes. Such genomic destabilization may thereby promote aging and carcinogenic processes.

Age-dependent genomic alterations have also been observed in the nuclear DNA of dividing cells. Genomic destabilization is observed through the incidence of tumorigenic mutations that strike genes involved in the control of cell proliferation, i.e., the protooncogenes and tumor suppressor genes. See, *Mutat. Res.*, Vol. 275, pp. 113–114 (1992). The principle of chemoprevention is the reduction in incidence of mutagenic events, thus preventing the onset of the carcinogenic process.

Mutagenesis, whether mitochondrial or nuclear in nature, is widely thought to be the result of the effect of reduced, reactive oxygen species and associated free radicals. Mitochondrial DNA is continually exposed to such oxy-radicals. The age-dependent decline in the capability and capacity of mitochondria to dispose of these reactive species eventually render mtDNA more vulnerable to mutagenic events during the aging process. Through a variety of proposed mechanisms, free radicals, whether generated by radiation or during normal cell respiration, have been shown in the prior art to induce a multitude of different DNA lesions in mammalian tissues, as well as in bacteria, and have also been implicated in carcinogenic processes. See, *Mutat. Res.*, Vol. 269, pp. 193–200 (1992).

Reactive oxygen species and related free radicals may be generated with equal effect through a variety of exogenous (environmental) or endogenous agents, the result of chemical or radiational insult and the like. Regardless of the origin or cellular mechanism, these mutagenic events are expressed through genome destabilization and eventual mutagenesis. Ionizing radiation is often employed in laboratory studies as a surrogate for other various environmental mutagenic agents. The propriety of such an assumption has been demonstrated in vitro using stock cultures of selected hamster cell lines which exhibited identical mutagenesis at the hypoxanthine-guanine phosphoribosyl transferase (HPRT) locus exposed to either ionizing radiation or cis-diaminedichloroplatinum (II). See, Grdina et al, *Cancer Research*, Vol. 46, pp. 1132–1135 (1986); and Grdina et al, *Int. J. Radiation Oncology Biol. Phys.*, Vol. 12, pp. 1475–1478 (1986).

The prior art is concerned with protecting against the genotoxic effects of radiation by the S-ω(ω-aminoalkylamino)alkyl dihydrogen phosphorothioates and has focused on the pre-irradiation effect of dosages on amelioration of radiation's lethal effects with no appreciation for the anti-mutagenic, but only mutagenic effects. In prior art uses, it was required to administer maximum tolerated levels of the drugs prior to radiation exposure. Such requirements have limited the effectiveness of these agents because, when administered at the required maximum tolerated dose, they are debilitating causing fever, chills, rash, hypotension, nausea and vomiting. It is conventionally accepted that the drugs must be administered prior to radiation exposure which heretofore has precluded their use for individuals accidentally exposed to radiation.

Since 1949, the status of the prior art dictates that, in order for the radioprotective drug to be effective, it must be present before radiation exposure. The conventional understanding is also that the disulfide form of radioprotectors is incapable of providing protection. In drugs such as WR-2721 the level of protection is proportional to the amount of the drug administered. The prior art also teaches there are potential mutational properties of these agents which must be avoided. In particular, it has been suggested that one such agent in this class of phosphorothioates identified as S-2(3-aminopropylamino) ethyl phosphorothioic acid (also known as "WR-2721"), by way of intracellular reactions, can lead to the conversion of cytosine moieties in DNA to uracil. The result of use of WR-2721 can then be a mutagenic reaction in normal tissue.

These above enumerated concerns, along with conventional wisdom existing since as long ago as 1949, have prevailed and have discouraged investigation into the potential of phosphorothioates and related aminothiol compounds as chemopreventative agents.

Radioprotection is distinguished from chemoprevention in that the former refers to protection against cell killing by irradiation and the latter refers to protection against mutagenic and related carcinogenic processes. Phosphorothioates and related compounds, when employed as radioprotectors, are operationally defined as materials which can protect against genotoxic damage induced by known mutagens and carcinogens occurring as a result of ionizing radiation administered after ingestion of the chemical agent or drugs. The accepted protective mechanisms of action of these drugs include: the scavenging of free radicals produced as a result of the radiolysis of cellular water (presumably, free radical damage to DNA); the repair of chemical lesions via hydrogen atom donation; and the induction of cellular hypoxia. The deleterious effects of radiation occur via the deposition of energy in less than $10^{-12}$ sec, while the relaxation of ionizations and excitations occur in less than $10^{-2}$ sec. Damage to DNA, which leads to cell lethality, is completed between $10^{-7}$ and $10^{-3}$ sec. These models are consistent with the failure to demonstrate protection against cell lethality by the phosphorothioates and related aminothiols when they are administered immediately following radiation exposure.

In 1985 it was reported that a free thiol designated 2-[(aminopropyl)amino] ethanethiol could protect against somatic mutations at the hypoxanthine-guauine phosphoribosyl transferase locus in cultured rodent cells (designated V79), even if it were administered 3 h following irradiation. These in vitro results relating to post irradiation exposure and protection by this agent against mutagenesis were extended in 1989 to include protection against fission-spectrum neutrons. The extreme toxicity of this agent precluded its testing under in vivo conditions to ascertain the actual anti-mutagenic effect in a mammal. In 1987 the drug cysteamine was tested as an antimutagen, but no protective effects were observed unless it was present during irradiation (administered prior to).

The problem of genome instability and subsequent mutagenesis is associated both with endogenous and environmental mutagenic agents, including cosmic radiation, ultra violet light, radiation from nuclear reactors and war-released materials, and radiation from diagnostic and therapeutic sources. The development of mutations and related carcinogenic and aging processes arising from these and like radiation sources are well-documented and proven to be major health risks to the population as a whole, as well as to high-risk groups employed in the nuclear power industry, military, and patients receiving diagnostic and therapeutic radiation treatments. Likewise, mutagenic events originate from a variety of chemical and chemotherapeutic agents.

There exists a need for a method for protecting against mutations irrespective of the source of mutagenic event or insult which will be amenable to pre- and/or post-radiation administration and which will be effective at relatively low non-toxic concentrations so as to allow use in mammals and also allow for multiple, as well as single, administrations.

Accordingly, it is an object of the present invention to provide a novel method and substance for reducing mutations of mammal cells, including humans, exposed to radiation or chemical insult and like mutagenic events.

It is another object of this invention to provide a method of and compositions for protection against mutagenesis, irrespective of the source of mutagenic event or insult, such that genome stabilization is provided and that aging and carcinogenic processes are inhibited.

It is another object of the invention to provide an improved method for use of aminothiols and associated metabolites which diminish mutation of both cancerous and normal cells exposed to radiation or chemotherapy and the like, whether administered before or after therapy.

It is an additional object of the invention to provide a method using S-ω(ω-aminoalkylamino)alkyl dihydrogen phosphorothioates to protect against initial mutagenic events irrespective of their source or nature and promote genome stabilization, such that subsequent mutagenesis and loss of genetic information is prevented.

It is still another object of the invention to provide a class of aminothiol agents which metabolize in vivo to produce free sulfhydryl groups and disulfides for protection against mutagenesis in mammalian cells.

It is a further object of the invention to provide a therapeutic route by which an aminothiol and/or aminodisulfide metabolite of a phosphorothioate agent is utilized to provide protection against mutagenic events and subsequent mutagenesis.

It is another object of this invention to provide a method for use of an antimutagenic agent to modulate cellular enzymatic processes, stabilize genomic material, prevent loss of cell function and genetic information, and increase the efficiency of and time available for cell repair processes.

It is still another object of this invention to provide a method for use in vivo of an antimutagenic agent to enhance the fidelity of mutational repair through delay of cell cycle progression or related cellular mechanisms.

It is a further object of this invention to provide a method for in vivo use of compositions which are both reactive toward the deleterious formation of free radical species by exogenous or endogenous sources and mitigate the mutational damage induced thereby, thus reducing the accumulation of genetic mutations as manifested through aging and carcinogenic processes.

These and other objects of the present invention will become apparent from consideration of the following description of preferred embodiments, examples, claims, and the drawings described below.

BRIEF DESCRIPTION OF THE DRAWINGS

FIG. 5A demonstrates the effect of cellular levels of 2-[(aminopropyl) amino] ethanethiol (i.e., WR-1065) and its disulfide (i.e., WRSS) on the protection against cell killing in FIG. 5B and protection against mutagenesis in FIG. 5C following irradiation with 150 cGy of fission-spectrum neutrons. Each error bar is one standard error of the mean;

FIG. 6A shows the structure of the disulfide form (designated WR-33278) of 2-[(aminopropyl) amino] ethanethiol (designated WR-1065) compared to the polyamine spermine (FIG. 6B);

FIG. 7A, FIG. 7B, FIG. 7C, FIG. 7D, FIG. 7E, FIG. 7F, FIG. 7G, FIG. 7H, FIG. 7I and FIG. 7J show the chemical structures of the phosphorothioates/aminothiols used;

S-[2-(3-methylaminopropyl amino ethyl] phosphorothioate (designated W-3689), S-1-(2hydroxy-3-amino) propyl phosphorothioic acid (designated (WR-77913); and 2-[3-methylamino) propylamino] ethanethiol (designated WR-255592) in protecting against radiation-induced mutagenesis. These results are shown as a function of administration either 30 min before or immediately after irradiation with 150 cGy of fission-spectrum neutrons. Each error bar is one standard error of the mean.

FIG. 10A, FIG. 10B, FIG. 10C, FIG. 10D, FIG. 10E, FIG. 10F, FIG. 10G, FIG. 10H, FIG. 10I, FIG. 10J, FIG. 10K, FIG. 10L, FIG. 10M, FIG. 10N, FIG. 10O, FIG. 10P and FIG. 10Q demonstrate the inhibition of topoisomerase IIα activity in CHO K1 cells by the administration of WR-1065, as either thiol- or disulfide-mediated.

FIG. 10A demonstrates the effects of WR-1065 and radiation on the activities of Topo I and IIα in K1 CHO cells, as determined by DNA relaxation and unknotting assays, respectively. Comparisons made to the corresponding untreated control groups using Student's two-tailed t test. Comparisons not significant, $p \geq 0.386$, except as noted. Topo I and Topo IIα expressed in units/μg protein (mean ±S.D. of four experiments). Topo IIα in K1 cells+WR-1065, −γ-ray, significant difference at $p=0.019$. Topo IIα in K1 cells +WR-1065 and +γ-ray, suggestive difference at $p=0.061$. FIG. 10B demonstrates the effects of WR-1065 and radiation on the protein levels of Topo IIα in K1 CHO cells, as determined by immunoblotting using an anti-Topo II specific antibody. Comparisons made to the corresponding untreated control groups using Student's two-tailed t test. All comparisons not significant, $p \geq 0.300$. Results expressed as mean ±S.D of at least three experiments. FIG. 10C demonstrates survival curves for K1 CHO cells irradiated with 50-kVp x-rays. Cells were either treated with 4 mM WR-1065 (■) or untreated (●). Experimental points represent the mean of three experiments; error bars represent the standard error of the mean. Survival curve parameters were determined by using a computer-fitted least-squares regression model. FIG. 10D and FIG. 10E show Topo IIα (FIG. 10D) and Topo I (FIG. 10E) activity in nuclear extracts from untreated and WR-1065-treated K1 cells. Nuclear extracts containing the following amounts of protein were assayed for Topo IIα-mediated unknotting and Topo I-mediated relaxing activities, as described herein: FIG. 10D, lane 1, 80 ng; lane 2, 40 ng; lane 3, 20 ng; lane 4, 10 ng; lane 5, 5 ng; FIG. 10E, lane 1, 100 ng; lane 2, 30 ng; lane 3, 10 ng; lane 4, 3 ng; lane 5, 1 ng; (−), no nuclear extract. This is a representative experiment. Data from four such experiments were used to determine the mean activities. FIG. 10F shows an immunoblot analysis of Topo IIα levels in nuclear extracts from untreated and WR-1065-treated K1 cells. Logarithmically growing cells were washed twice by centrifugation at 1000×g for 5 minutes in PBS containing protease inhibitors and extracts. Nuclear proteins were subjected to gel electrophoresis through an 8% SDS-polyacrylamide gel and transferred to nitrocellulose. Blots were incubated with anti-Topo II antibody. The molecular weights shown on the right ordinate are those of Topo IIα (MW 170,000) and its proteolytic products. Prestained standards with their molecular weights in thousands are shown on the left ordinate. Lane 1, untreated cells; lane 2, WR-1065-treated but unirradiated cells, lane 3; irradiated cells; lane 4, cells irradiated and treated with WR-1065. FIG. 10G shows an immunoblot analysis of Topo IIα levels in rapidly lysed cells. Conditions were similar to those described with the exception that cells were lysed in electrophoresis sample buffer containing 2% SDS by boiling for 2 minutes. FIG. 10H and FIG. 10I show Topo I (FIG. 10H) and Topo IIα (FIG. 10I) activity in cell-free extracts. Reaction mixtures were assayed for Topo I-mediated relaxation of pUC8 plasmid DNA and Topo IIα-mediated unknotting of P4 phage DNA, as described herein: FIG. 10H, lane 1, pUC8 DNA only; lane 2, no drug; lane 3, 0.4 mM WR-1065; lane 4, 4 mM WR-1065; lane 5, 40 mM WR-1065; lane 6, 0.5 mM Camptothecin. FIG. 10I, lane 1, no drug; lane 2, 0.4 mM WR-1065; lane 3, 4 mM WR-1065; lane 4, 40 mM WR-1065; lane 5, 0.3 Genistein. FIG. 10J, FIG. 10K, FIG. 10L, FIG. 10M, FIG. 10N, FIG. 10O, FIG. 10P and FIG. 10Q show typical flow cytometry patterns describing the DNA distribution of K1 cells exposed to 4 mM WR-1065for 0 min (FIG. 10J), 30 min (FIG. 10K), 1.0 hour (FIG. 10L), 2.0 hours (FIG. 10M), 3.0 hours (FIG. 10N), 4.0 hours (FIG. 10O), 5.0 hours (FIG. 10P) and 6 hours (FIG. 10Q). During the 6 hour exposure, the percent of cells in G1 fell from 39 to 21, while the percent of cells in G2 increased from 18 to 27. The percent of cells in S ranged from 43 to 46.

FIG. 12A, FIG. 12B, FIG. 12C, FIG. 12D, FIG. 12E, FIG. 12F, FIG. 12G and FIG. 12H illustrate the anti-mutagenic effect of WR-33278 electroporated into CHO AA8 cells. (FIG. 12A and 12B). Effects of WR-33278 (open bar) and spermine (hatched bar) on CHO AA8 cell survival (FIG. 12A) and mutation induction at the hprt locus (FIG. 12B). Drug-only bars represent the effects of 0.01 mM WR-33278 or 0.01 mM spermine on these processes. FIG. 12A: compared with its corresponding drug exposure only group, all cell survivals in each of the electroporated groups are significantly reduced (student's two-tailed t test, $p \geq 0.001$). FIG. 12B: compared with its corresponding drug exposure only group, the number of mutants per $10^6$ surviving cells in each of the electroporated groups is not significantly different ($p \leq 0.01$). Data presented are from a minimum of 3 replicate experiments. Error bars represent one standard error of the mean. FIG. 12C and FIG. 12D. Effect of electroporation on radiation-induced cell killing (FIG. 12C) and mutagenesis at the hprt locus (FIG. 12D). FIG. 12C: as compared with cell killing by radiation only, cell survival was significantly reduced by electroporation performed 30 min. before ($p=0.007$) or 3 hours after $p>0.001$) irradiation. FIG. 12D: mutation induction was significantly enhanced by electroporation performed 30 min. before ($p>0.001$) or 3 hours after ($p>0.001$) irradiation. Experiments were repeated a minimum of 3 times. Error bars represent on standard of the mean. FIG. 12E and FIG. 12F. Effects of electroporation with either WR-33278 (open bars) and spermine (hatched bars) on the survival of cells irradiated with 750 cGy either 30 min. after (FIG. 12E) or 3 hours before (FIG. 12F) electroporation. FIG. 12E: comparing electroporation with no drug 30 min. prior to irradiation, electroporation of 0.01 mM WR-33278 or spermine 30 min. prior to irradiation significantly protected against cell killing (p=0.006 and p=0.013, respectively). Electroporation of 0.001 mM WR-33278 or spermine was less effective (p=0.25 and p=0.02, respectively). FIG. 12F: comparing electroporation with no drug 3 hours after irradiation, electroporation of WR-33278 did not affect cell survival (0.01 mM, p=0.1; and 0.001 mM, p=0.1). Electroporation of spermine at a concentration of 0.01 mM was more effective p=0.01) than a concentration of 0.001 mM p=0.23). All experiments were repeated a minimum of 3 times. Error bars equal one standard error of the mean. FIG. 12G and FIG. 12H. Effect of electroporation with either WR-33278 (open bars) or spermine (hatched bars) on hprt mutation induction in cells irradiated with 750 cGy either 30 min. after (FIG. 12G) or 3 hours before (FIG. 12H) electroporation. FIG. 12G: comparing electroporation with no drug 30 min. prior to irradiation, electroporation of both 0.01 mM and 0.001 mM WR-33278 or spermine were highly effective in protecting against the induction of hprt mutants (p>0.001, p=0.015, p>0.001, p=0.04, respectively). FIG. 12H: comparing electroporation with no drug 3 hours following irradiation, electroporation of both 0.01 mM and 0.001 mM WR-33278 or spermine were highly effective in protecting against the induction of hprt mutants (all p values>0.001). All experiments were repeated a minimum of 3 times. Error bars represent one standard error of the mean. FIG. 12I, FIG. 12K and FIG. 12K illustrate the role performed by the presence of an amine funtionality, as evidenced through a comparison of 1-cysteine and N-acetylcysteine (FIG. 12I: 1-cysteine; MEC-41, 43; FIG. 12J: N-acetyl-1-cycteine; MEC-40, 42; FIG. 12K: N-acetyl-1-cycteine; MEC-40). Each error bar is one standard error of the mean.

FIG. 18 is a differential display of different DNA's separated on a sequencing gel, with the patterns of gene expression compared. Fourteen bands were identified that exhibited altered expression following WR-1065 treatment. The bands exhibiting the largest changes are identified by the superimposed boxes.

FIG. 19 is a sequence comparison of the differential display of WR-Band 13(Q) to the 3'UT regions of mouse (M), human (H), and published CHO (CHO), Thymidine kinase genes. Underlined sequences make up the Poly A signal. Nucleotides in bold are those shared with WR-Band 13 and other tk 3' UTR sequences. Sequences are based on those of Lin et al. for mouse (41), Lewis for CHO (42) and Bradshaw and Deininger (43) for human.

FIG. 21, WR-2721 effects on cytoxan-induced cytotoxicity and mutagenesis. FIG. 21 is a table summarizing data demonstrating that low dosages of WR-2721 can prevent HPRT (hypoxanthine-guanine phosphoribosyl transferase) mutagenesis without affecting the therapeutic effects of cytoxan on the killing of mouse fibrosarcoma tumor cells growing in the lungs of mice. HPRT mutant frequency expressed as mutants per $10^5$ viable cells.

DESCRIPTION OF THE PREFERRED EMBODIMENTS

The present invention is concerned with four general areas: (1) phosphorothioates and associated metabolites, when administered to mammals (i.e., mice) following mutagen exposure (i.e., ionizing radiation including photon and fission-spectrum neutrons and chemical mutagens such as cisdiaminedichloroplatinum (II) (cisplatin) and cytoxan), protect against genotoxic damage which normally leads to the development of somatic mutations—the same mutations observed in human lymophocytes; (2) protection against mutagen-induced mutations by the phosphorothioates and associated metabolites at very low concentrations which are much less than required for protection against cell lethality; (3) protection against mutagen-induced somatic mutations by the phosphorothioates and associated metabolites, as shown to correlate most closely with the disulfide metabolite and the presence of a polyamine functionality; and (4) protection against mutagen-induced somatic mutations, as a general property of the genus of phosphorothioates and their associated metabolites irrespective of the origin of the mutagenic event; all of which are demonstrated by the observed antimutagenic properties of the species S-1-(aminoethyl)phosphorotinoic acid (WR-638), S-[2-(3-methylaminopropyl) aminoethyl] phosphorothioate (WR-3689), S-2-(4-aminobutylamino) ethylphosphorothioic acid (WR-2822), 3-[(2-mercaptoethyl)amino]propionamide p-toluenesulfonate (WR-2529), S-1-(2-hydroxy-3-amino) propyl phosphorothioic acid (WR-77913), 2-[3-(methylamino) propylamino] ethanethiol WR-255591), S-2-(5-aminopentylamino) ethyl phosphorothioic acid (WR-2823), and 1-[3-(3-aminopropyl) thiazolidin-2-yl]-D-gluco-1,2,3,4,5 pentane-pentol dihydrochloride (WR-255709).

I. Phosphorothioate Genus Protection After Irradiation.

Figure 1:
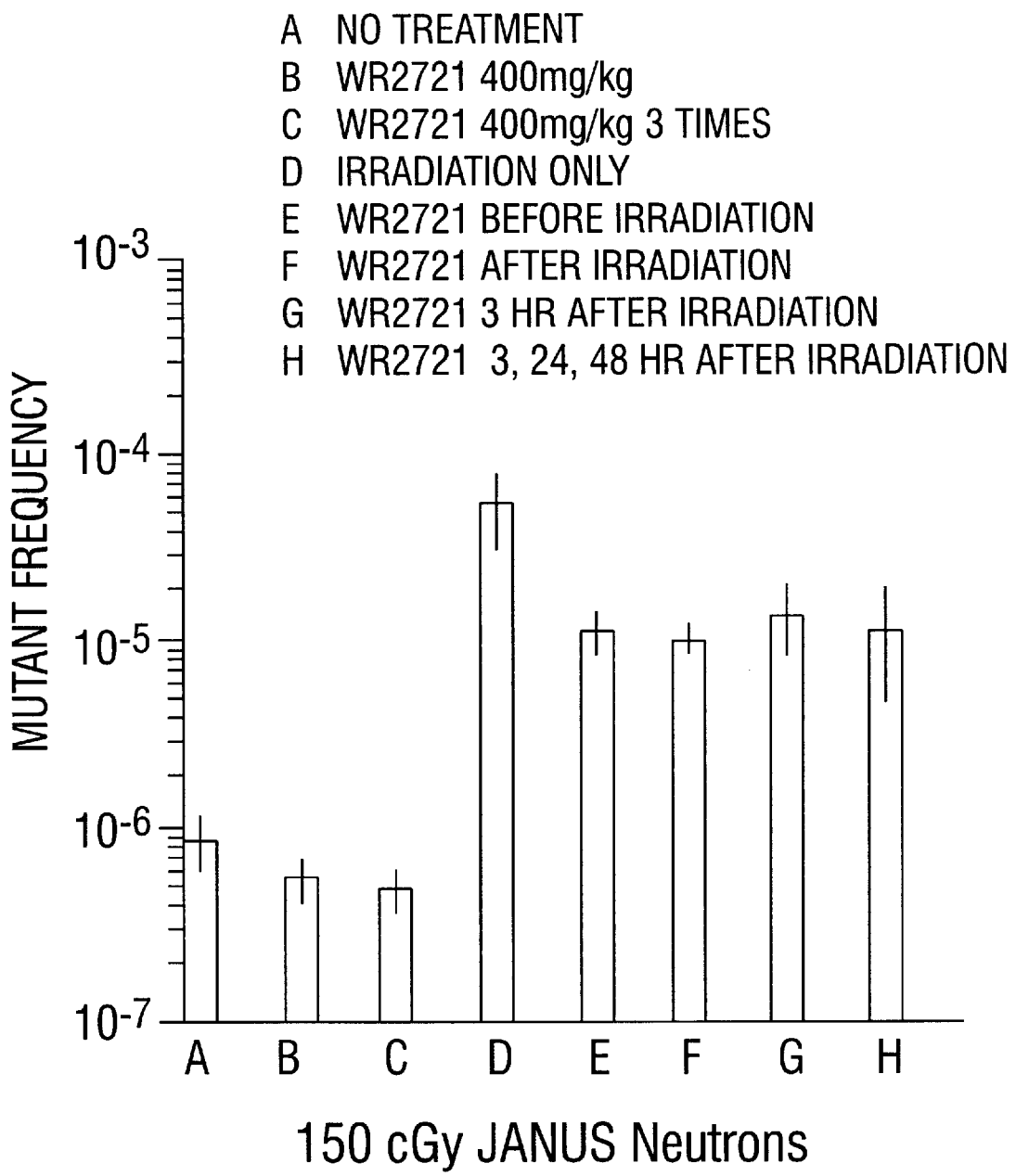
FIG. 1 demonstrates the performance of S-2-(3-aminopropylamino) ethylphosphorothioic acid (also identified as WR-2721) to protect against radiation-induced mutagenesis when administered to animals either 30 min before, immediately after, or 3 h following irradiation. Error bars represent one standard error of the mean.

Chemicals of the phosphorothioate genus and associated metabolites can protect against somatic mutations when administered to mammals following a mutagen exposure. This conclusion is based on the observation that S-2-(3-aminopropylamino)ethyl phosphorothioic acid, administered at a dose of 400 mg/kg up to 3 h following neutron radiation exposure, affords substantial protection against radiation-induced mutations at the hypoxanthine-guanine phosphoribosyl transferase locus in the T lymphocytes of mice (see FIG. 1, ref. 10). The magnitude of protection is unchanged regardless of whether the phosphorothioate was administered 30 min before, immediately following (i.e., within 10 min), or up to 3 h following irradiation of the test animals.

It will be understood by those skilled in the art and made aware of this invention that dosage units of mg/kg of body weight can be converted and expressed in comparable concentration units of μg/ml or mM (blood levels). It is also understood that uptake after administration is species and organ/tissue dependent. The applicable conversion factors and physiological assumptions to be made concerning uptake and concentration measurement are well-known and would permit those of skill in the art to convert one concentration measurement to another and make reasonable comparisons and conclusions regarding the doses, efficacies and results described herein. By way of example only, in mice given 100 mg/kg of WR-2721, 30-minute blood levels are reported at 49 μg/ml or 0.23 mM. Accordingly, a 400 mg/kg mouse dose would correspond to a concentration of WR-2721 of about 1.0 mM. Likewise, a human subject given about 740 mg/m$^2$ of WR-2721 (by IV infusion) would have an initial plasma level at about 100 μmol/liter or 0.1 mM.

The spontaneous mutant frequency of T lymphocytes from unirradiated control animals was stable and ranged from 9–10×10$^{-7}$. Following irradiation with 150 cGy of fission neutrons, the mutant frequency increased to 5.6×10$^{-5}$±2.3×10$^{-5}$ (1 standard error of the mean). Mutant frequencies in animals administered S-2-(3-aminopropylamino) ethylphosphorothioic acid 30 min before immediately after, or 3 h following irradiation with 150 cGy of fission neutrons were 1.1×10$^{-5}$±2.6×10$^{-6}$, 1.0×10$^{-5}$±1.3×10$^{-6}$, and 1.4×10$^{-5}$±5.8×10$^{-6}$, respectively.

As stated above, the aminothiol 2-[(aminopropyl)amino]ethanethiol (WR-1065) is the active thiol of S-2-(3-aminopropylamino)ethylphosphorotioic acid (WR-2721). Aminothiols, such as WR-1065 and its associated disulfide metabolite, are effective in inhibiting DNA synthesis, strand rejoining, nuclease activity, and cell cycle progression in mammalian cells. These effects on cellular enzymatic processes indicate aminothiol protection against mutagenesis includes modulation of endogenous enzyme processes relating to DNA synthesis and repair. WR-1065 is an effective radiation protector and antimutagenic agent when it is administered 30 min prior to radiation exposure to Chinese hamster ovary K1 cells (i.e., a dose modification factor of 1.4) at a concentration of 4 mM. Under these exposure conditions, topoisomerase (topo) I and IIα activities and associated protein contents were measured in the K1 cell line using the DNA relaxation assay, the P4 unknotting assay, and immunoblotting, respectively. WR-1065 was ineffective in modifying topo I activity, but it did reduce topo IIα activity by an average of 50 percent. The magnitude of topo IIα protein content, however, was not affected by these exposure conditions. (See FIG. 10A–FIG. 10I). Cell cycle effects were monitored by the method of flow cytometry. Exposure of cells to 4 mM WR-1065 for a period of up to 6 h resulted in a buildup of cells in the G2 compartment. (FIG. 10J–FIG. 10Q.) This observed cell cycle delay in conjunction with reduction in topo IIα activity indicates more time available for the repair of cell damage and suggests genome stabilization and increased efficiency of repair processes.

These results demonstrate, in particular, a modifying effect by 2-[(aminopropyl)-amino]ethanethiol on type II topoisomerase, which is involved in DNA synthesis. In contrast to typical topo II inhibitors used in chemotherapy, WR-1065 and/or its disulfide are effective agents against both radiation-induced cell lethality and mutagenesis. At concentrations up to 40 mM, WR-1065 did not affect the activity of either topo II or topo IIα, as compared to inhibitors Camptothecin and Genistein, suggesting, without being bound to any one theory or mechanism of operation, that WR-1065-induced reduction in topo IIα activity may be due to some indirect effect. Without limitation, this observation may involve inhibition of protein kinase C-mediated metabolic phosphorylation of topo IIα by WR-1065. Inhibiting phosphorylation could reduce the activity of enzymes that serve as substrates for this protein kinase. This possible mode of action is consistent with the observed reduction in the catalytic activity of topo IIα and WR-1065-treated K1 cells (determined by the unknotting assay), without a concomitant reduction of topo IIα protein levels (determined by immunoblotting).

The topoisomerase studies demonstrate the ability of phosphorothioates and associated metabolites to influence cellular response to mutagenic insult and cellular enzymatic activities involved in DNA synthesis, cell cycle progression and, possibly, repair.

Figure 13:
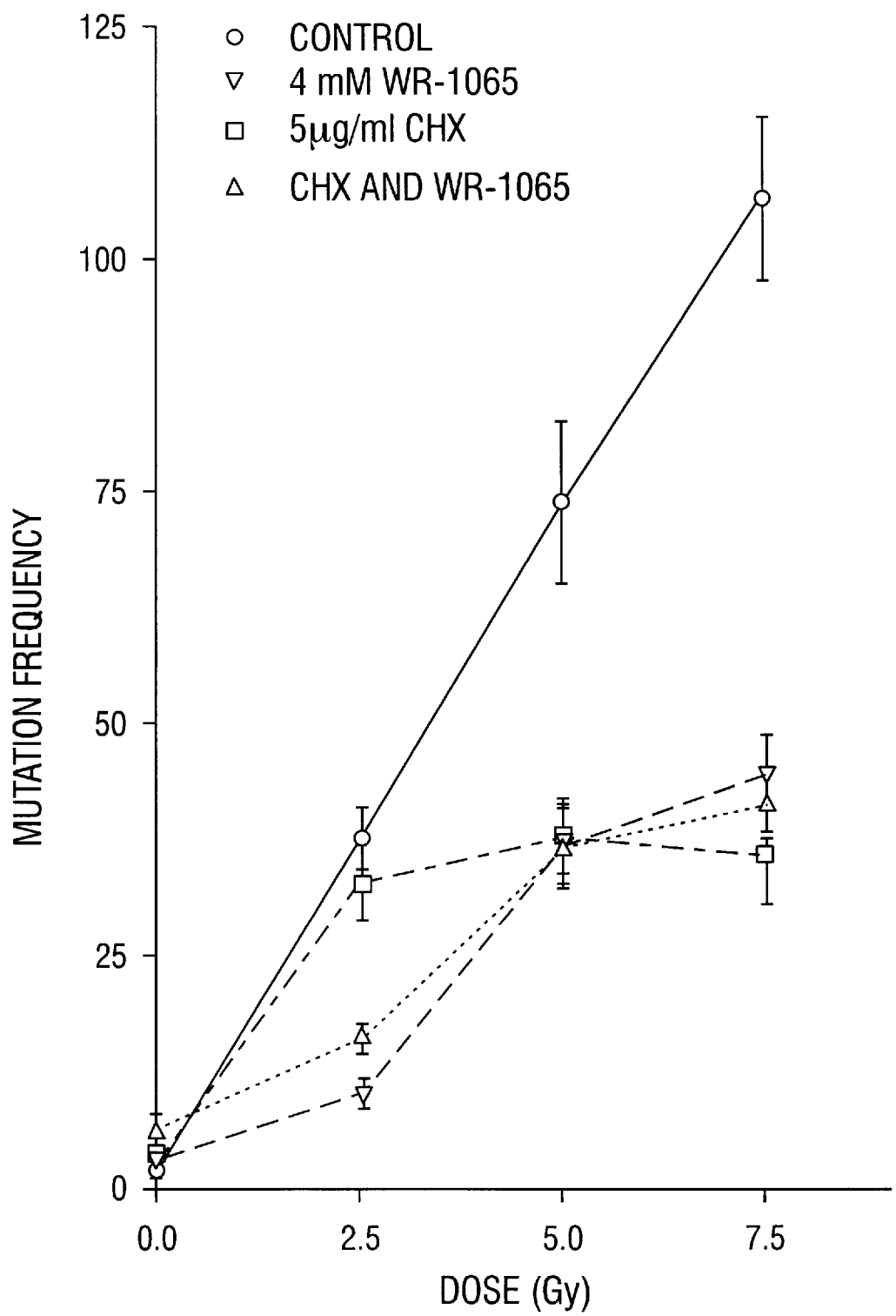
FIG. 13 graphically represents the pretreatment of cells for 30 minutes as shown, with cycloheximide alone, WR-1065 alone, and the combination of both agents with respect to protection against radiation induced mutagenesis prior to radiation exposure.
Figure 14:
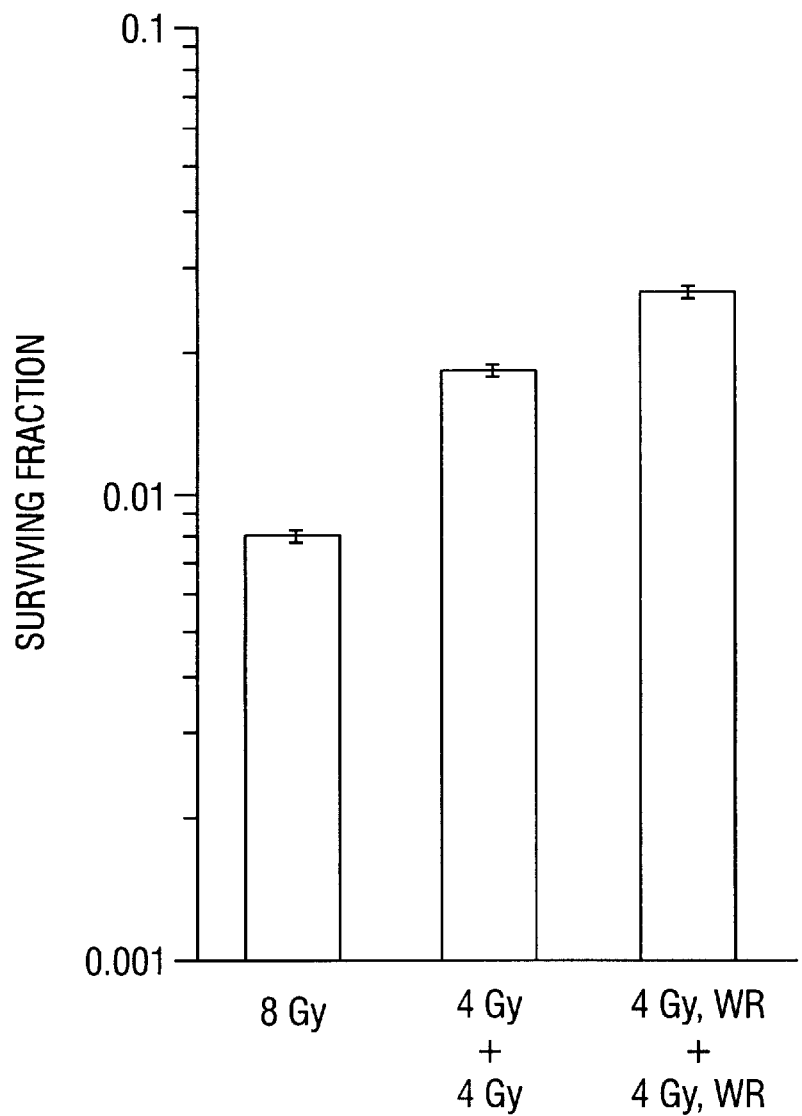
FIG. 14 illustrates enhanced cell survival with WR-1065 treatment and concomitant reduction in mutagenesis, in contrast to cycloheximide treatment.
Figure 15:
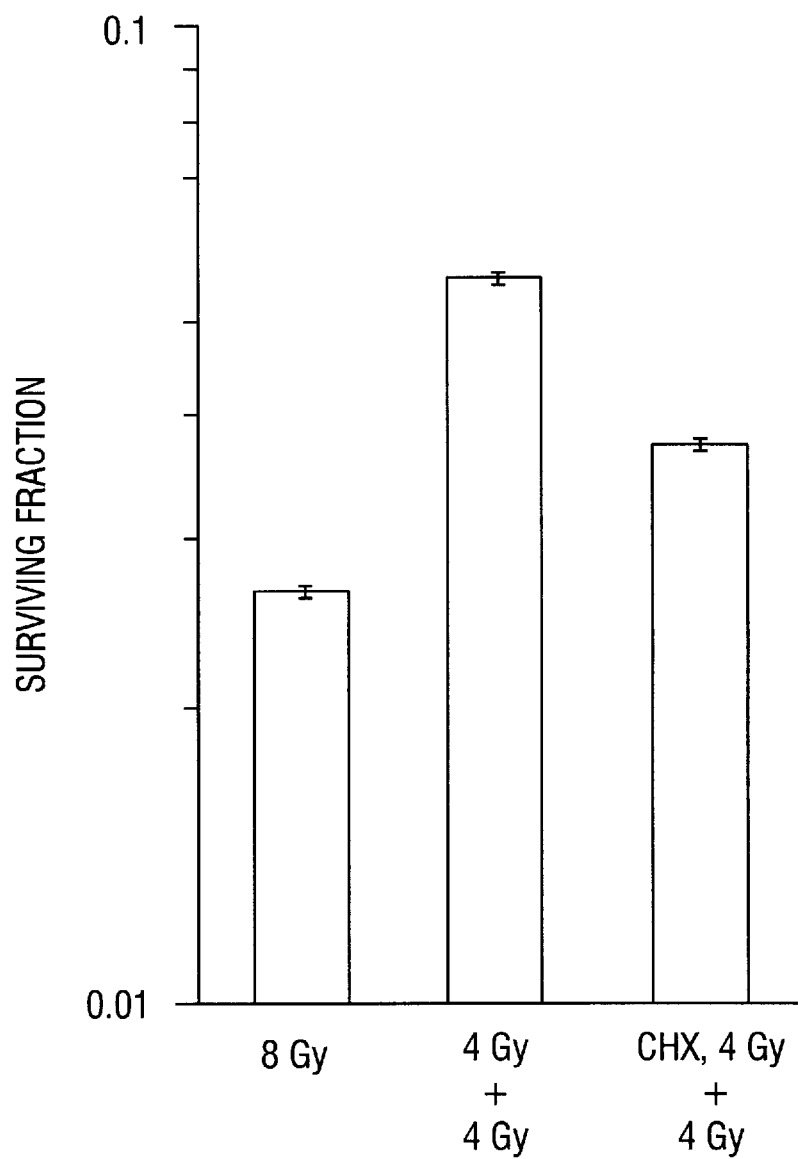
FIG. 15 illustrates the effects of the split dose methodology, as described more fully below.
Figure 16:
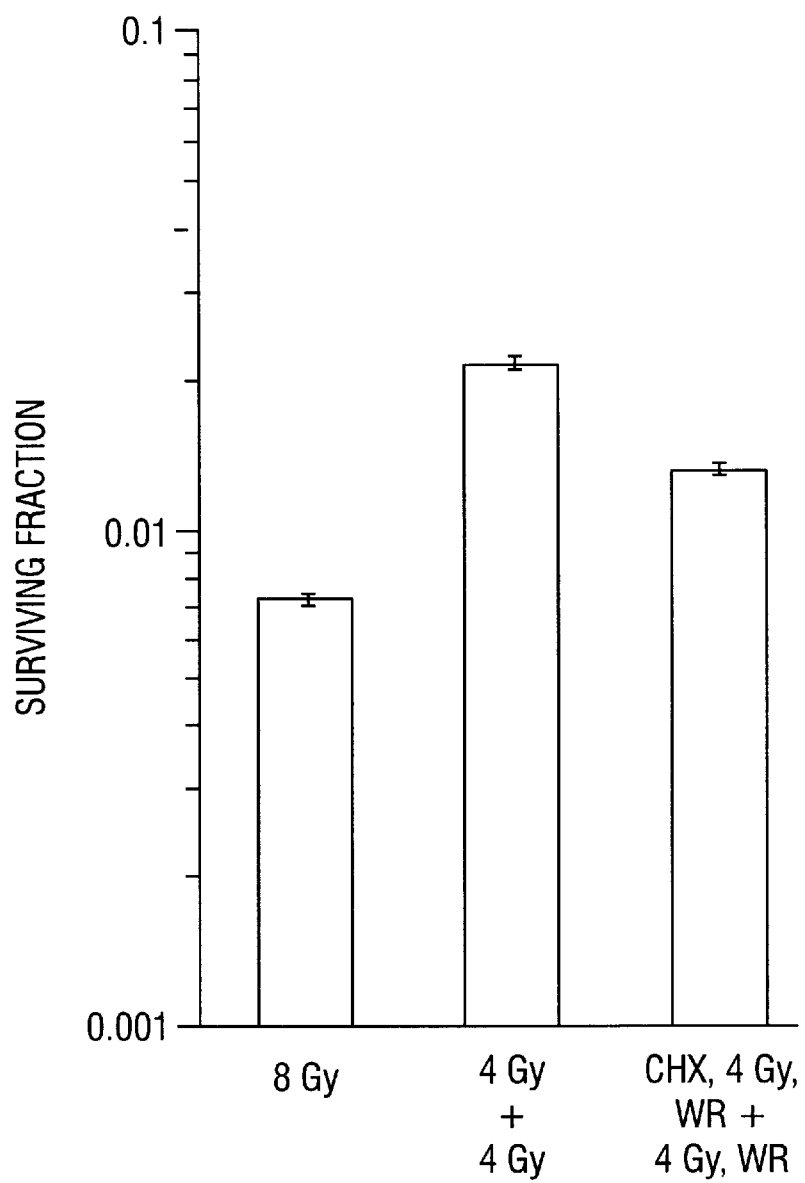
FIG. 16 illustrates treatment with cycloheximide followed by treatment with WR-1065 inhibits the effect of WR-1065.
Figure 17:
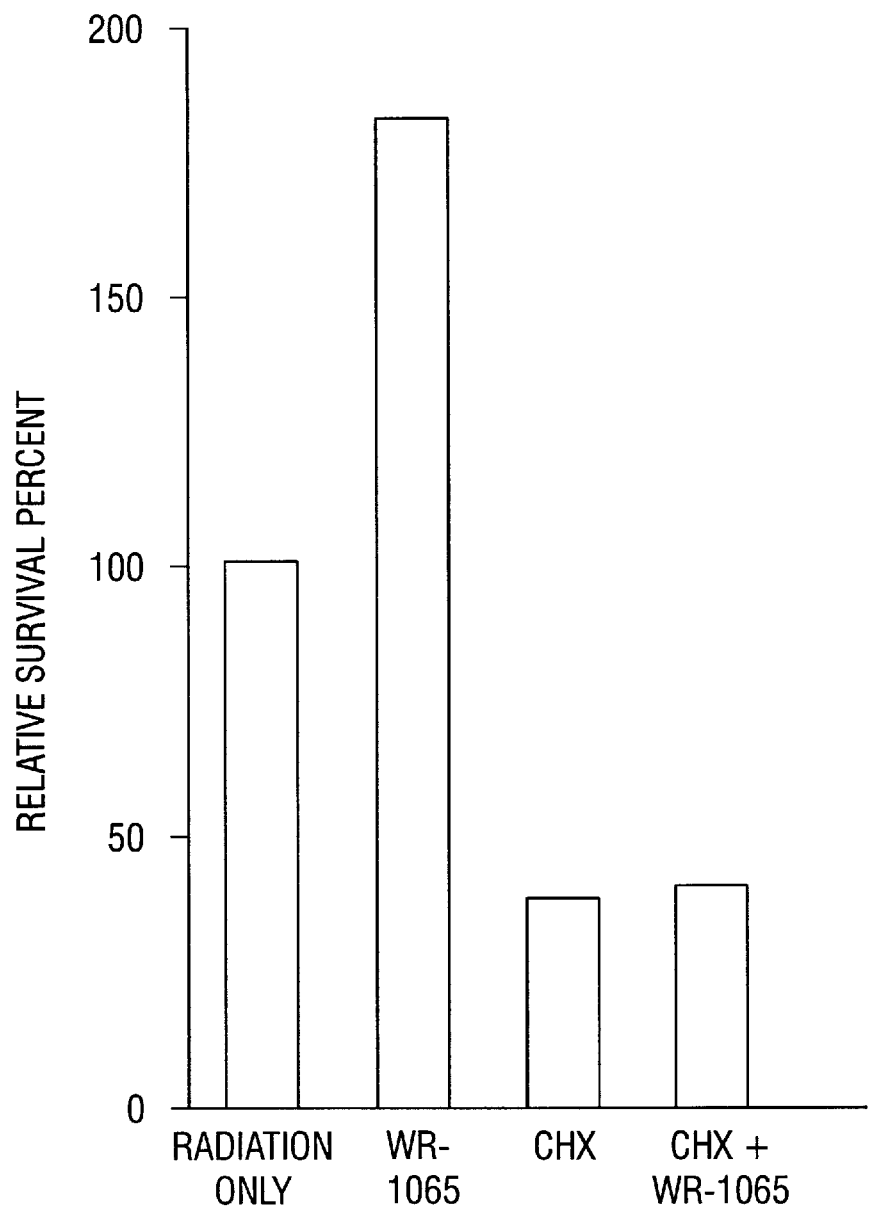
FIG. 17 presents a summary of normalized data from FIGS. 14, 15 and 16, by way of comparison.

The ability of WR-1065 and its disulfide WR-33278 (both forms of the drug are measured intracellularly following WR-1065 exposure of cells and therefore both may play a role in protection), to affect radiation and/or drug induced mutagenesis when administered following treatment suggests that they are affecting an inducible error-prone repair system. Studies using cycloheximide in conjunction with WR-1065 were carried out to address this issue. As described in FIG. 13 pretreatment of cells for 30 min with 4 mM WR-1065 with or Without concomitant treatment with 5 μg/ml of cycloheximide (CHX) resulted in protection against radiation induced mutagenesis under all conditions tested. The magnitude of protection appeared to be the same regardless of whether cells were exposed to WR-1065 alone, CHX alone, or the combination of both agents. CHX is known to inhibit an inducible error prone repair system and as a result will protect against mutagenesis. To compare and contrast the effects of CHX with WR-1065 a series of split dose experiments were performed. Presumably, if protection against mutagenesis can only be attributed to the inhibition of an inducible error-prone repair system, inhibition of that system will give rise to a reduced mutation frequency as well as a reduced cell survival. To address these issues CHO AA8 cells in exponential growth phase were exposed to 8 Gy of radiation only; 8 Gy of radiation followed by a 30 min exposure to 4 mM WR-1065; 4 Gy of radiation only; 4 mM WR-1065 for 30 min and then washed free of drug before 4 Gy of radiation; 4 Gy followed by 4 h of incubation at 37° C. and then an additional dose of 4 Gy; 4 Gy of radiation followed by 30 min treatment with 4 mM WR-1065, an additional 3½ h of incubation after washing off the drug, followed by 4 Gy and then an additional 30 min post-irradiation treatment with WR-1065; 5 μg/ml CHX for 30 min prior to 4 Gy with a continued 4 h exposure to 5 μg/ml CHX followed by an additional 4 Gy dose of radiation and an additional 30 min exposure to CHX (5 μg/ml); and a combination treatment of 5 μg/ml CHX 30 min prior to 4 Gy followed by 30 min exposure to both WR-1065 (4 mM) and CHX (5 μg/ml), wash out drugs and continue with 3½ h exposure to 5 μg/ml CHX only followed by an additional 4 Gy, and 30 min post-irradiation exposure to 4 mM WR-1065 and 5 μg/ml CHX. Post-irradiation treatment of cells with 4 mM WR-1065 did not affect the survival of cells exposed to a single dose of 8 Gy (FIG. 13). Cells exposed to WR-1065 for 30 min and then washed free of the drug before exposure to 4 Gy exhibited no change in cell survival (i.e., WR, 4 Gy vs 4 Gy). WR-1065, however, enhanced cell survival when it was present after each radiation dose during the split dose repair experiments (i.e., 4 Gy+4 Gy vs 4 Gy, WR+4 Gy, WR). In contrast to the single dose survival data, WR-1065 can enhance cell survival under split dose conditions, presumably by enhancing the ability of an inducible repair system to repair radiation damage. These data are plotted in FIG. 14 for comparison. Cycloheximide (CHX) did not affect cell survival to single doses but it inhibited split dose repair as evidenced by a reduction in the survival of cells (i.e., 4 Gy+4 Gy vs CHX, 4 Gy+CHX, 4 Gy) (FIG. 15). When combined with WR-1065, CHX treatment inhibited the protective effect of WR-1065 (i.e., 4 Gy +4 Gy vs CHX, 4 Gy, WR+CHX, 4 Gy, WR) (FIG. 16). This effect is similar to that reported for the protein synthesis inhibitor chloramphenicol on cysteamine-mediated protection in *E. coli* cells. The relative effects of WR-1065, CHX, and CHX+WR-1065 on cell survival following split dose exposures are presented in FIG. 17 for comparison. The data obtained for CHX is consistent with the literature. The current model is that protein synthesis is required for the induction of an error prone repair system which if inhibited will give rise to both a lower mutation frequency and a lower cell survival level. This model does not adequately describe the protective effects of WR-1065. Presumably, while WR-1065 does not affect protein synthesis nor the induction of an error prone repair system, it is capable of interacting with such a system to enhance its fidelity of repair. Without limiting the scope of this invention or adopting any particular theory or mode of operation, it is thought that by virtue of their polyamine like structure, aminothiols can concentrate within the nucleus and stabilize the complex on which the repair proteins work, i.e., the damaged sites on DNA.

Figure 20:
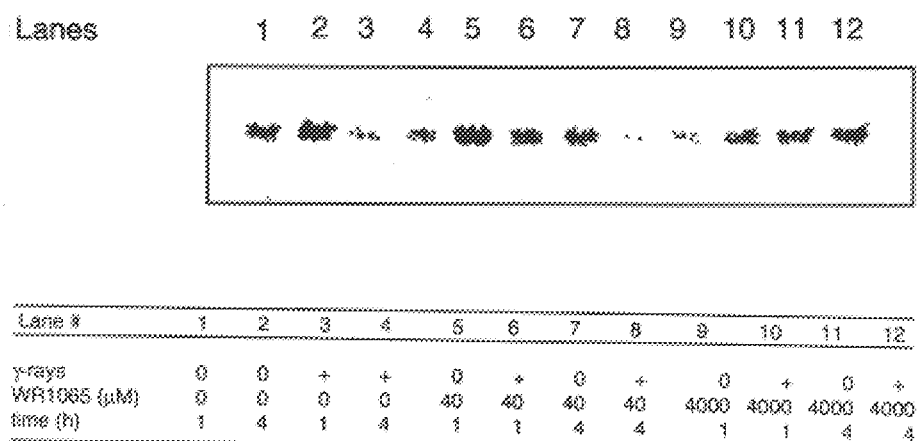
FIG. 20 shows the results of a Northern blot analysis confirming the data from the differential display, establishing that radiation represses tk MRNA expression in CHO cells (lanes 1, 2 vs 3, 4). This repression is made less dramatic by the presence of 40 $\mu$M WR-1065 (lanes 5, 7 vs 6, 8) and in fact expression becomes enhanced when cells are pretreated with 4 mM WR-1065 (lanes 9, 11 vs 10, 12). This suggests that tk gene expression can be affected by WR-1065. It is important to note that this response may be cell line specific since we have not tested it in other cell lines.

By way of investigating use of the present invention in conjunction with clinically-relevant intermediate biomarkers for chemoprevention, RNA was extracted from untreated cells as well as from cells exposed to radiation alone, radiation in combination with either 4 mM or 40 $\mu$M WR-1065, and WR-1065 alone. A dose of 4 mM WR-1065 is required to demonstrate radiation protection against cell killing. Since WR-1065 can scavenge free radicals as well as chelate metal co-factors needed for enzymatic activity, a dose of 4 mM may affect a number of cellular systems that may not be evident at more physiological lower doses. For this reason we also investigated a dose of 40 $\mu$M which, while not protective against cell killing, is known to be effective in protecting against radiation-induced mutagenesis. Different cDNAs were made and amplified using a $T_{11}$ CA anchored primer and two different tenmers ($R_2$= TCTAGTGAGG; and R3=CCTGCACTAC). These were separated on a sequencing gel and the patterns of gene expression were compared. We identified 14 bands that exhibited altered expression following WR-1065 treatment (see FIG. 18). Bands exhibiting the largest changes are identified by the superimposed boxes. Some bands were repressed while others were induced following exposure to WR-1065. Bands were screened by dot blot hybridization and levels of expression were compared by phosphoroimaging. The results revealed that differential display and dot blot hybridization were consistent for 9 of the 14 bands. Bands were sequenced using an automated sequencer (Applied Biosystems) and compared to sequences available in GenBank and EMBO and Japanese sequence databases. Sequence homologies were found for two unidentified genes from macrophage and infant brain cDNA libraries. Two bands were found to have up to 70% identity with mouse lamin A, one had over 80% identity with PCTAIRE-1 (a mouse protein kinase similar to yeast cdc2), and another shared common sequences with the 3'UT region of the mouse thymidine kinase gene (see FIG. 19). Thymidine kinase was also verified by Northern analysis (see FIG. 20). The other bands have not yet shown any homology to known cDNAs and may represent new gene sequences. Probes for a number of genes including catalase, plasma glutathione peroxidase, and cytosolic glutathione peroxidase were also supplied. For all of the genes with known homology, northern blots are presently being examined to confirm the expression patterns evident in both differential display and dot blot analyses and also comparing the size of the transcripts to those reported for these gene sequences.

It is interesting that the lamin genes (identified by two different bands) were induced following radiation exposure, but the expression was repressed by both concentrations of radioprotector. Lamins are nuclear proteins important in determining nuclear matrix association and structures that have been shown to be repressed in v-src transformed cells. The fact that WR-1065 represses the radiation-mediated induction of lamin transcripts may be related to the mechanism of action of the protector, especially regarding nucleoid structures. Thymidine kinase appears to be induced by WR-1065 4 h following treatment regardless of whether the cells are irradiated or not. Exposure to radiation actually represses the induction partially. The functional significance of this induction is not clearly known, though it may be related to cell cycle effects since thymidine kinase is regulated as cells progress through the cell cycle. The induction of a newly identified serine/threonine protein kinase, PCTAIRE-1 by exposure to radioprotector was also noted. This induction is evident within the first hour following treatment with 40 $\mu$M (but not 4 mM) WR-1065 whether or not the cells have been irradiated. This protein is interesting since it has such high identity in the 3'U T region to cdc2/CDC28 protein kinases. These proteins have been shown in other cell systems to be important in regulating cell cycle progression, and WR-1065 has been shown in past work by our group to affect cell cycle progression of irradiated cells.

As demonstrated above, the genes and their products shown to be regulated following exposure of cells to potential chemopreventive agents and radiation treatments and can be used as biomarkers for monitoring chemoprevention. It is anticipated that most of the gene products could be relatively quantified from a small sample (5–10 ml) of peripheral blood using either enzyme assays (for thymidine kinase and perhaps other kinases) or RT-PCR (for any of the transcripts), as well as for PCTAIRE-1, lamin, or thymidine kinase.

As would be recognized by those skilled in the art, the following is a description of the materials and methodologies used in demonstrating the utility of the present invention and its efficacy for the purposes and advantages described herein.

Cells and Culture Conditions. The Chinese Hamster Ovary cell line designated CHO-AA8 was used throughout this study. Cells were grown in alpha-minimal essential medium ($\alpha$-MEM) (Gibco, Grand Island, N.Y.) with 10% fetal bovine serum (FBS) (Biologos, Naperville, Ill.) in a humidified atmosphere containing 5% $CO_2$ and 95% air at 37° C. All experiments were performed with cells in the exponential phase of growth.

Irradiation Conditions. Cell suspensions were irradiated at room temperature with $^{60}Co\gamma$ rays from a $\gamma$-beam 650 irradiator (Atomic Energy of Canada).

Drug Treatment. WR1065 used in theses studies was supplied by the Drug Synthesis and Chemistry Branch, Division of Cancer Treatment, National Cancer Institute, and was made up in phosphate buffered saline (PBS) (8.1 mM Na$_2$HPO$_4$–1.4 mM KH$_2$PO$_4$–0.14M NaCl–2.6 mM KCl) at a 1-M concentration and sterilized by filtration immediately before use.

RNA Preparation. RNA was prepared by isolation in 6M guanidine isothiocyanate, extraction with phenol, and precipitation from 3M NaOAc, pH 6.0 (26). RNA was quantitated by monitoring absorbance at 260 nM. DNAse treatment of total RNA was done according to Liang et al. (1993). 50 µg of total RNA were incubated for 30 min at 37° C. with 10 units of DNAase I (Boeringer) in 10 mM Tris HCl pH 8.3, 50 mM KCI, 1.5 mM MgCl$_2$. After phenol extraction RNA was ethanol precipitated.

Primers. The following primers were used for the differential display leading to identification of tk transcript reported here: two 3' primers: (T)$_{12}$MA:TTTTTTTTTTMA and (T)$_{12}$MC:TTTTTTTTTTTMC; and one 5' primer: R3:CTTGATTGCC.

Reverse Transcription and PCR Reactions. RNA template was mixed with 20 pM of (T)$_{12}$MC or (T)$_{12}$MA primer in a total volume of 19 µl of 1×reaction buffer (50 MM Tris HCl pH 8.3, 75 mM KCI and 3 mM MgCl$_2$), 20 µM dNTP, 10 mM DTT; and incubated 5 min at 65° C. followed by 10 min at 37° C. M-MLV reverse transcriptase (Gibco-BRL) was added (200 units per sample) and mix incubated for 50 min at 37° C. Enzyme inactivation incubation was 5 min at 95° C.().

PCR with Labeled Primer(s). For each single reaction, 4 µl of labeled primer nix was added to 10 pM of cold primer and 1 µl of reverse transcription mix in 1×PCR reaction buffer (10 mM Tris HCI pH 8.3, 50 mM CKI, 1.5 mM MgCl$_2$ and 0.001% gelatin) and 2 µM to 200 µM dNTP in the presence of 0.5µ AmpliTaq enzyme (Perkin Elmer). The total volume of the reaction was 10 µl. One drop of mineral oil was added, and PCR reaction performed in Perkin Elmer Cetus Thermal Cycler. PCR parameters were 94° C. for 30 sec, 40° C. for 2 min, 72° C. for 30 sec with 40 cycles, followed by 5 min elongation at 72° C.

Primer Labeling. For a single PCR reaction a maximum of 10 pM of primer was labeled. The reaction mix with a final volume of 5 µl included: 10 pM of oligonucleotide, 6 pM of γ[$^{32}$P]ATP (3000 Ci/mmol; New England Nuclear) in 1×kinase buffer (50 mM Tris-Cl pH 8, 10 mM MgCl$_2$, 5 MM DTT, 0.1 mM spermidine, 0.1 mM EDTA) with 2 units of T4 polynucleotide kinase (Promega). Reaction mixture was incubated 45 min at 37° C., followed by 5 min enzyme inactivation at 95° C.

Gel Electrophoresis of DNA Fragments. After PCR samples were mixed 5:2 with formamide/dye "stop" solution (United States Biochemical Corp.), the mixture was heated at 80° C. for 2 min and cooled to 0° C. for at least 5 min before coating. Four µl aliquots were run on standard sequencing (0.45 mm thick) denaturing gels (6% Hydro Link Long-Ranger, 42 g urea per 100 ml gel, 1×Tris-borate buffer, 0.05% ammonium persulfate, 50 µl TEMED per 100 mL gel) on 50 W for 3.5 h, in 0.6×Tris-borate buffer.

Sequencing. PCR reaction was performed using conditions described above. The sequencing reaction was performed with PRISM Ready reaction dideoxy terminator cycle sequencing kit according to the manufacturer's instructions and with mode 370A automated sequencing machine (Applied Biosystems).

DNA-excess Dot Blots. Total RNA was analyzed following the method described by Wolosehak et al. (31) Briefly, 0.5 µg of double-stranded, cloned, plasmid DNA was resuspended in 1M ammonium acetate. The samples were dotted onto nitrocellulose filters using a dot-blot apparatus attached to a vacuum pump. The filters were washed in 3×SSC (45 mM Na citrate, pH 7.4, 0.45M NaCl), soaked for 1 h at room temperature in 1×Denhardt's solution (0.2% ficoll, 0.2% bovine serum albumin, 0.2% polyvinylpyrrolidone, 3×SSC), and then baked in a vacuum oven at 80° C. for 2 h. Prior to hybridization, filters were washed for 2 h at 55° C. in hybridization buffer (50% formamide, 1×Denhardt's solution, 10 µg/mL Poly A, 50 µg/mL herring sperm DNA, 3×SSC).

Ten micrograms of total RNA (as determined by A260) was partially hydrolyzed with NaOH and neutralized with HCI. The RNA was incubated at 37° C. for 45 min with 12 units of T4 polynucleotide kinase (Boehringer Mannheim Biochemicals, Indianapolis, Ind.) and 50 µCi of γ-$^{32}$P-labeled ATP (3000 Ci/mmol, NEN, Boston, Mass.). Unincorporated $^{32}$P-ATP was separated from RNA by Sephadex G25 column chromatography (Boehringer Mannheim Biochemicals, Indianapolis, Ind.) in 3×SSC at room temperature. The labeled RNA was denatured by incubation at 90° C. for 1 min and cooled on ice for 5 min. The RNA was hybridized to nitrocellulose filters dotted with DNA probes at 50° C. overnight. Filters were washed three times for 1 h in 3×SSC at 65° C. and three times 1 h each in 0.1×SSC at 65° C. Filters were dried and set up in the exposure cassettes over night. Storage phosphor plates were scanned on a PhosphorImager (Molecular Dynamics, Sunnyvale, Calif.).

Northern blots. RNA was separated by using formaldehyde agrose gel electrophoresis as a described previously (26). RNA samples (10 µg) were denatured in 50% fomamide, 1.9M formaldehyde 0.2M MOPS, 50 mM NaOAc, 1 mM Na$_2$EDTA (pH 7.5) for 15 min at 55° C., then separated on 1.2% agarose gels in 0.2M MOPS, 50 mM NaOAc, 1 mM NA$_2$EDTA, 2.2M formaldehyde. Mouse rRNA and RNA ladder (BRL Laboratories, Bethesda, Md.) markers were stained with ethidium bromide and photographed under ultraviolet light for use in sizing.

Northern transfers were performed as described (26). Blots were hybridized to $^{32}$P-nick-translated or oligolabeled cDNA probes. Hybridization conditions were 50% deionized formamide, 0.75M NaCl, 75 mM sodium citrate, 25–50 mM sodium phosphate (pH 6.5), 0.2% bovine serum albumin, 0.2% ficoll, 0.2% polyvinylpyrrolidone, and 50 µg/ml sonicated denatured herring sperm DNA at 43° C. Prior to hybridization, all labeled probes were heatlike this denatured at 90° C. for 5 min. After hybridization, nonspecific binding was reduced by washing the hybridized blots three times for 1 h each at 43° C. in 45 mM sodium citrate (pH 7.4), 0.45M NaCl, 0.2% ficoll, 0.2% polyvinylpyrrolidone, 0.2% bovine serum albumin, 50 µg/ml herring sperm DNA (sonicated, denatured), and 0.1% SDS, then three times for 1 h each in 1.5 mM sodium citrate (pH 7.4). 15 mM NaCl 50 µg/ml herring sperm DNA (sonicated, denatured), and 0.1% SDS. The blots were then dried and exposed to X-ray film at −20° C.

Figure 11A:
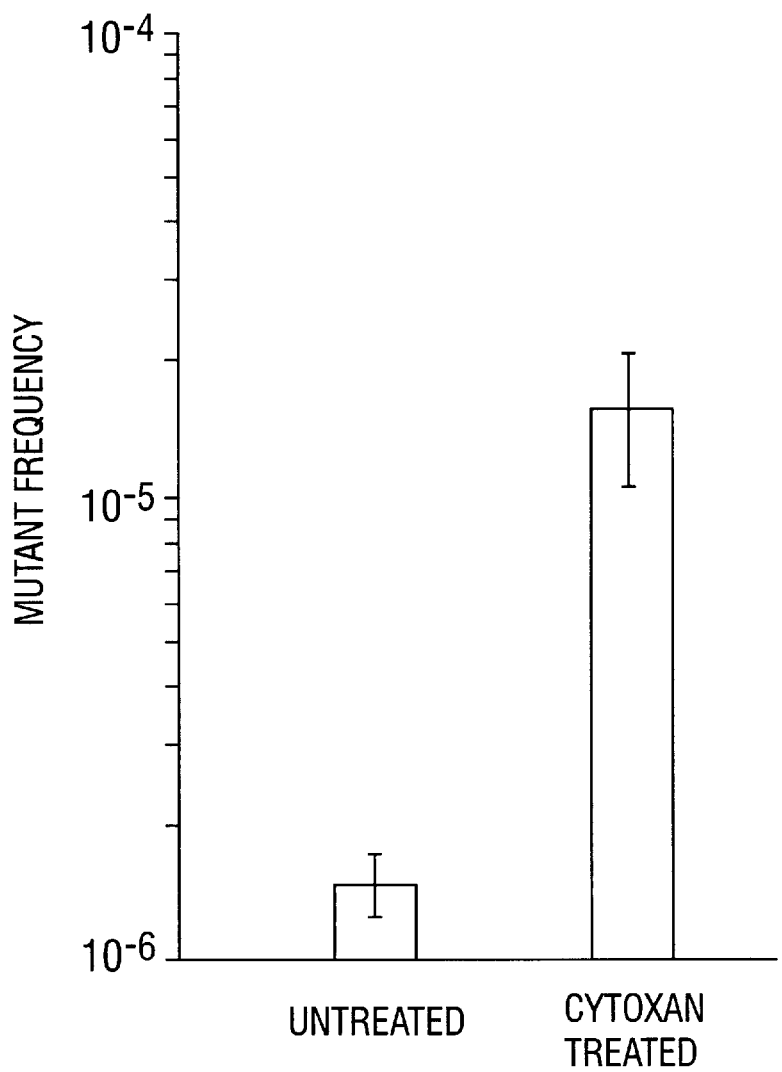
FIGS. 11A, 11B, FIG. 11C and FIG. 11D demonstrate the identity in mutations observed in both mouse and human T-lymphocytes at the HPRT locus, upon treatment with cytoxan—as is also observed after irradiation. The anti-mitagenic effect of WR-2721 and/or its associated metabolites was demonstrated in mice treated with cytoxan or cisplatin. Each error bar is one standard error of the mean.
Figure 11B:
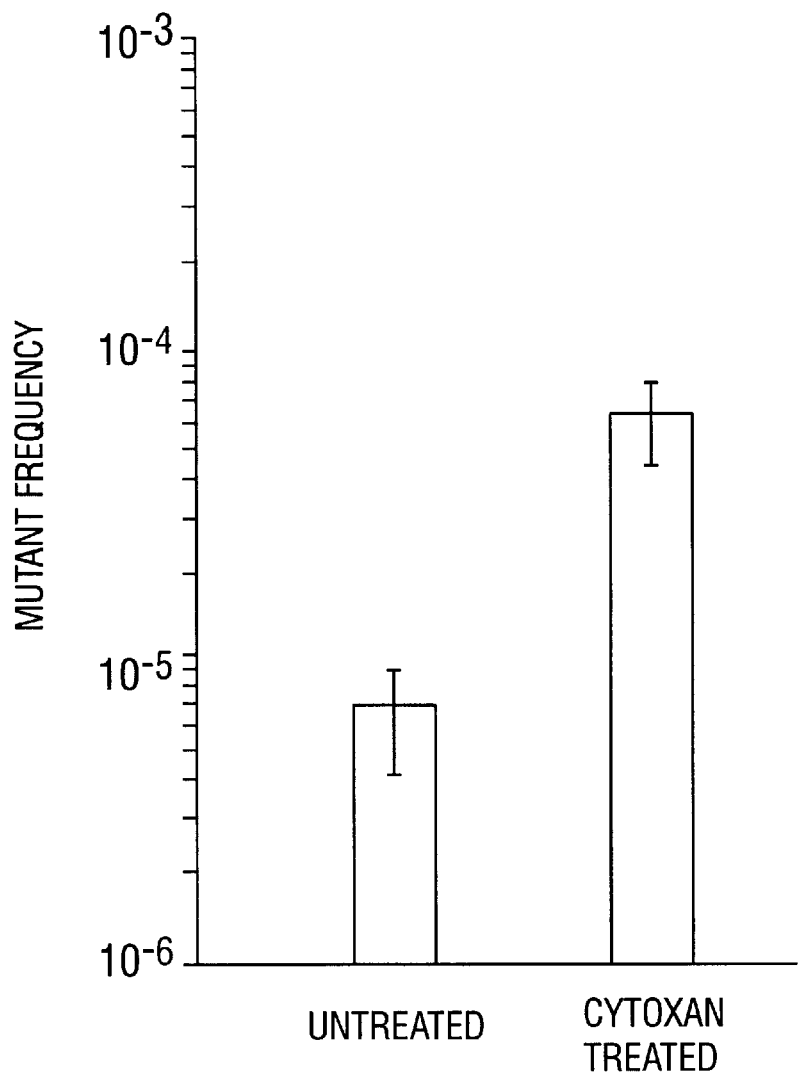

Referring to FIGS. 11A and 11B, mice and human cancer patients, respectively, were treated with cytoxan and observed with respect to the increase in mutant frequency. As shown, in comparison with untreated populations, both the mouse and human subjects exhibited substantial cytoxan-induced mutations at the hypoxanthine-guanine phosphoribosyl transferase (hprt) locus—consistent with the radiation-induced mutagenesis, described above, and supporting the proposition that the same mutation is observed irrespective of the nature and/or source of the mutagenic event. The mutant frequencies of mice T-lymphocytes were determined as described above. The human lymphocytes were obtained from blood samples of patients after the cytoxan treatment, using standard cell stimulation techniques and hprt assays.

Figure 11C:
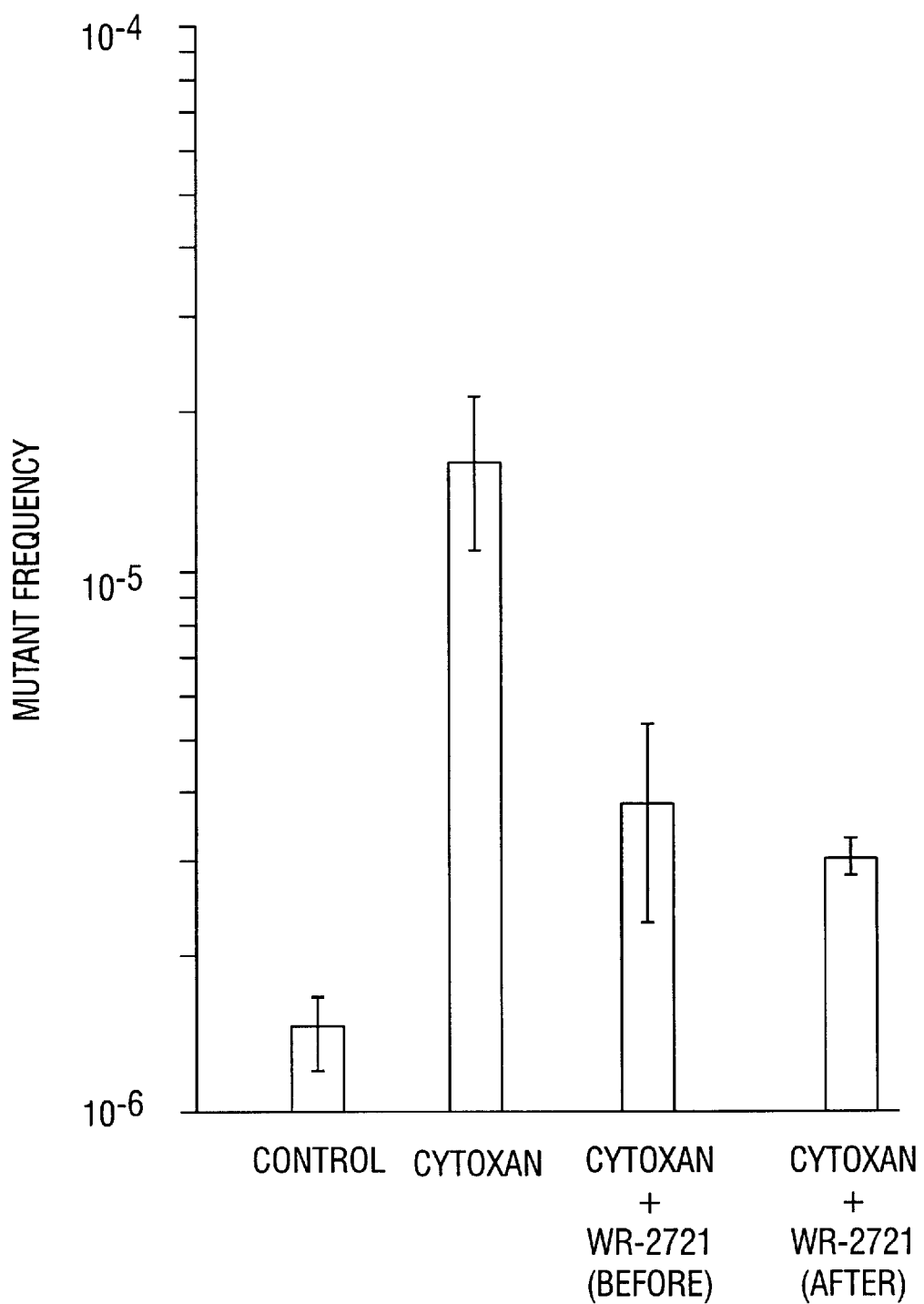
Figure 11D:
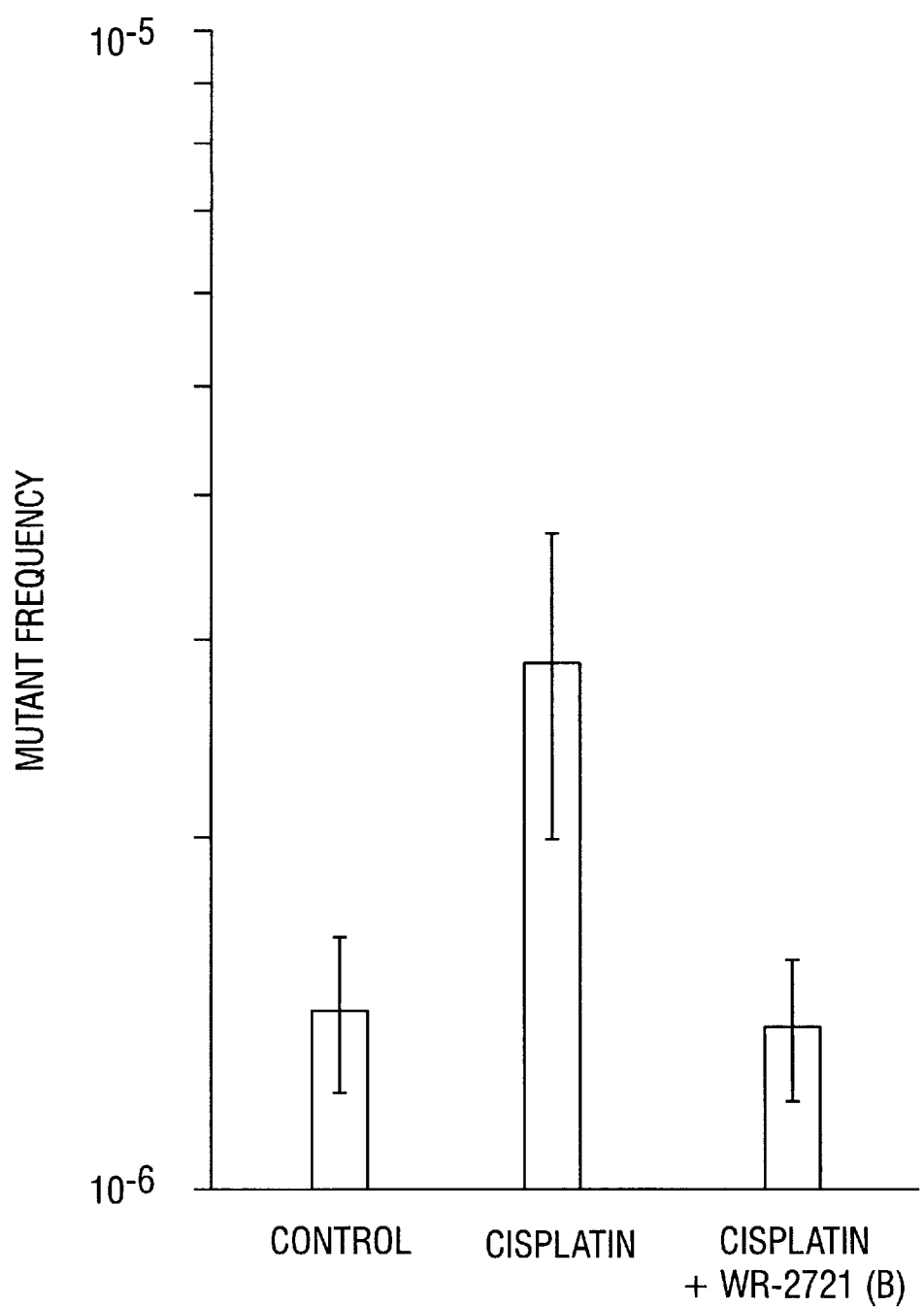
Figure 12A:
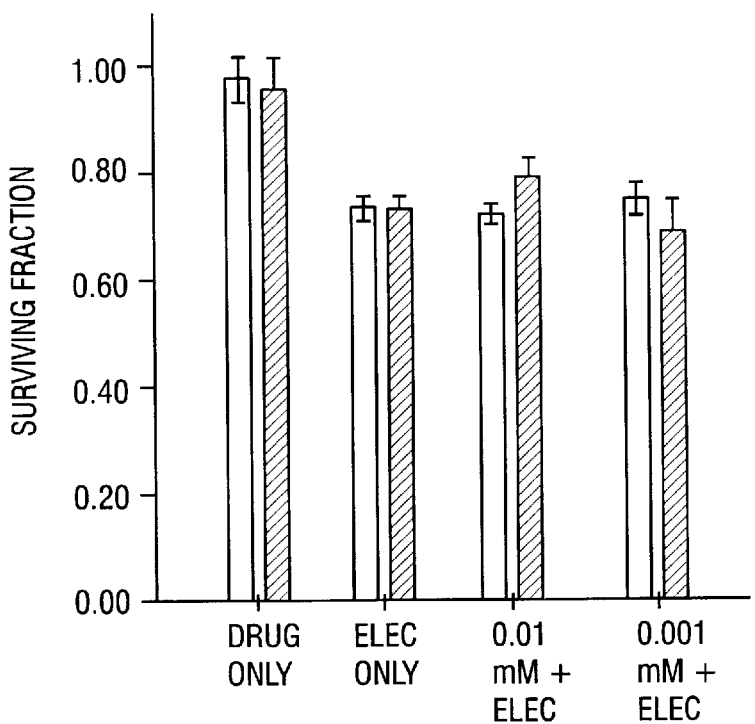
FIG. 12A, FIG. 12B, FIG. 12C, FIG. 12D, FIG. 12E, FIG. 12F, FIG. 12G, FIG. 12H, FIG. 12I, FIG. 12J and FIG. 12K.
Figure 12B:
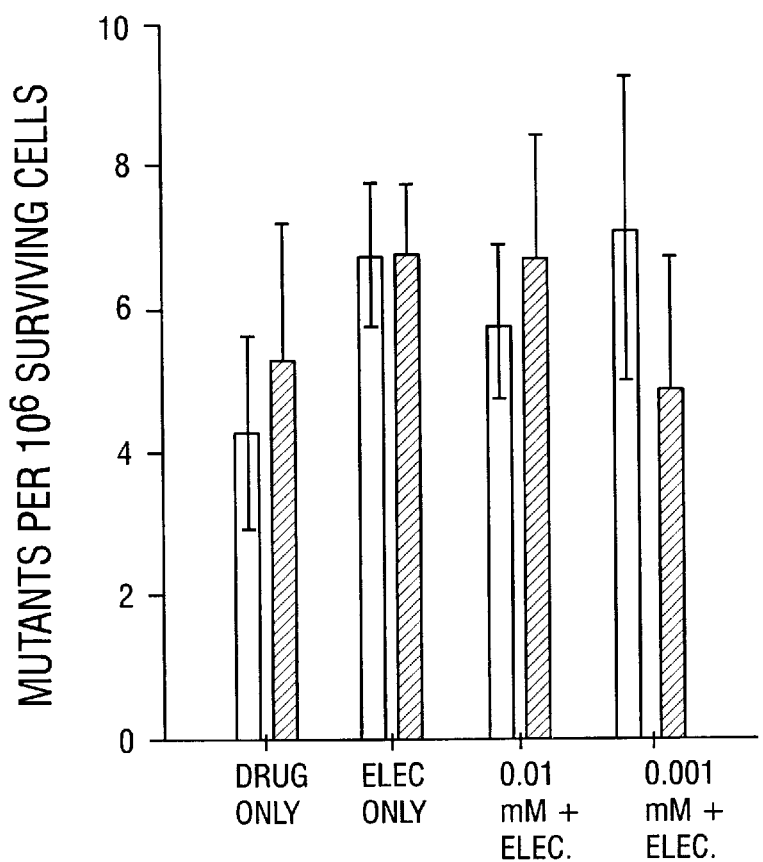
Figure 12C:
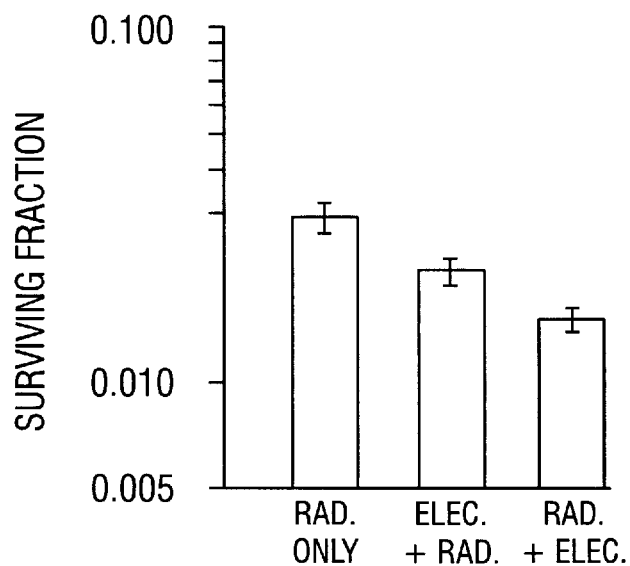
Figure 12D:
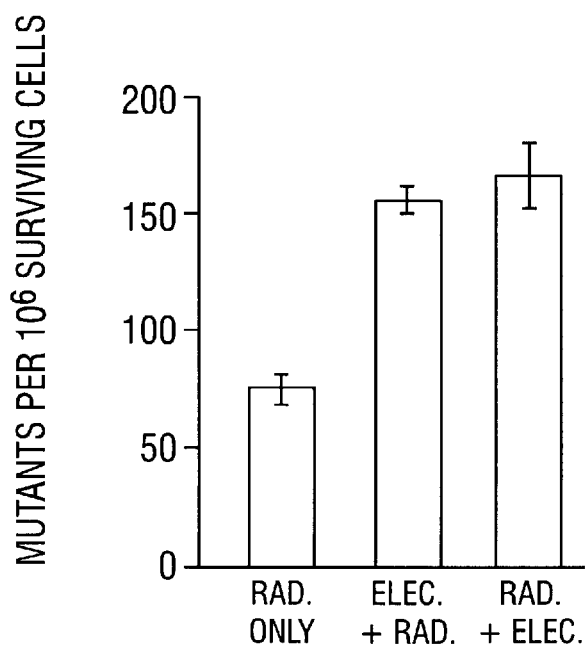
Figure 12E:
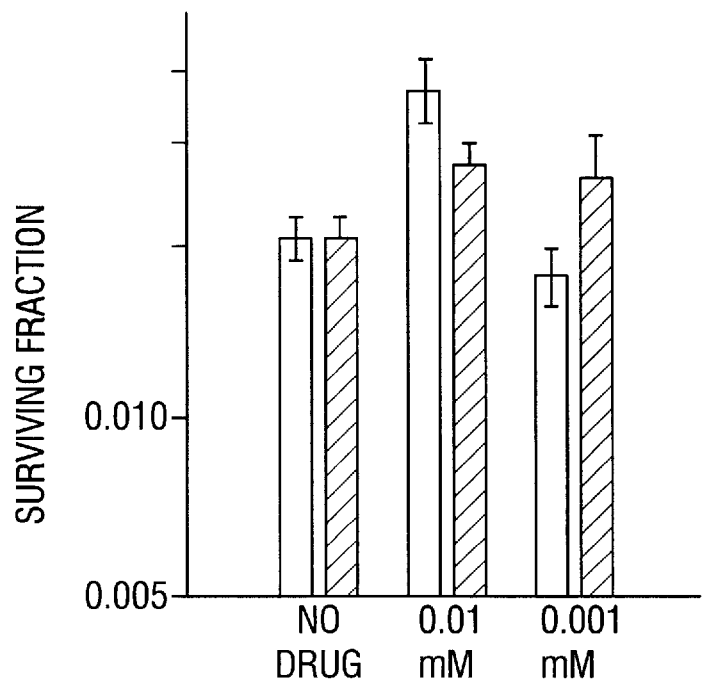
Figure 12F:
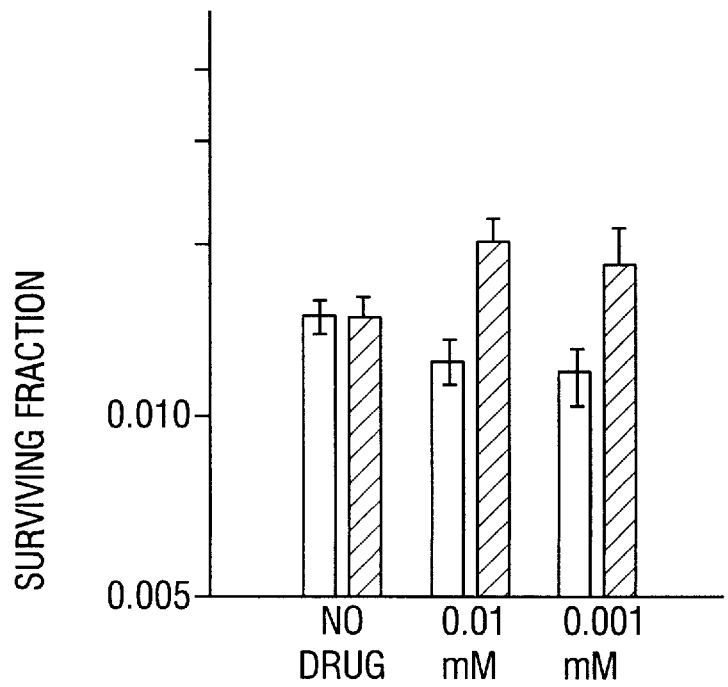
Figure 12G:
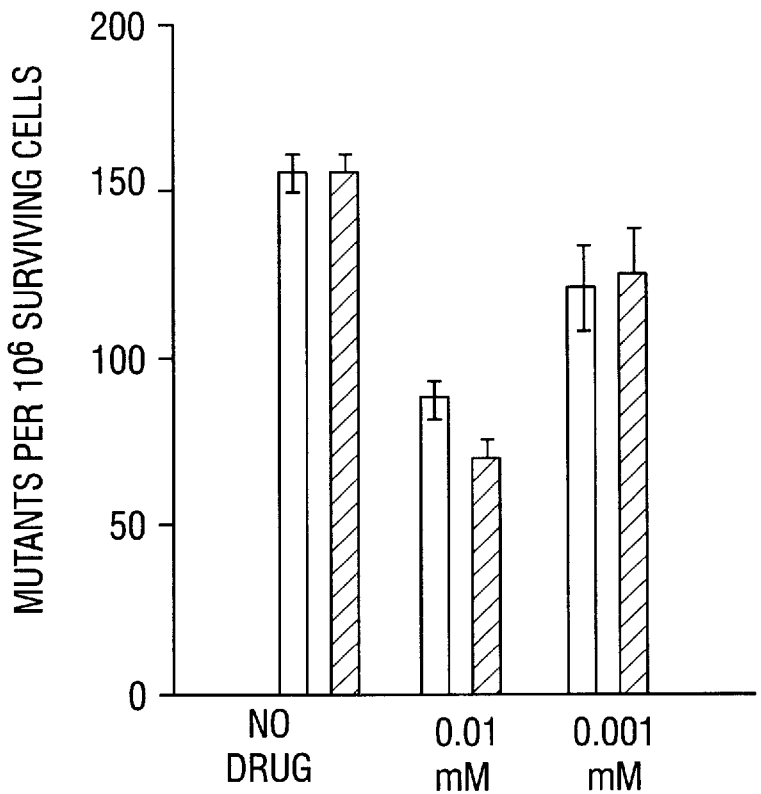
Figure 12H:
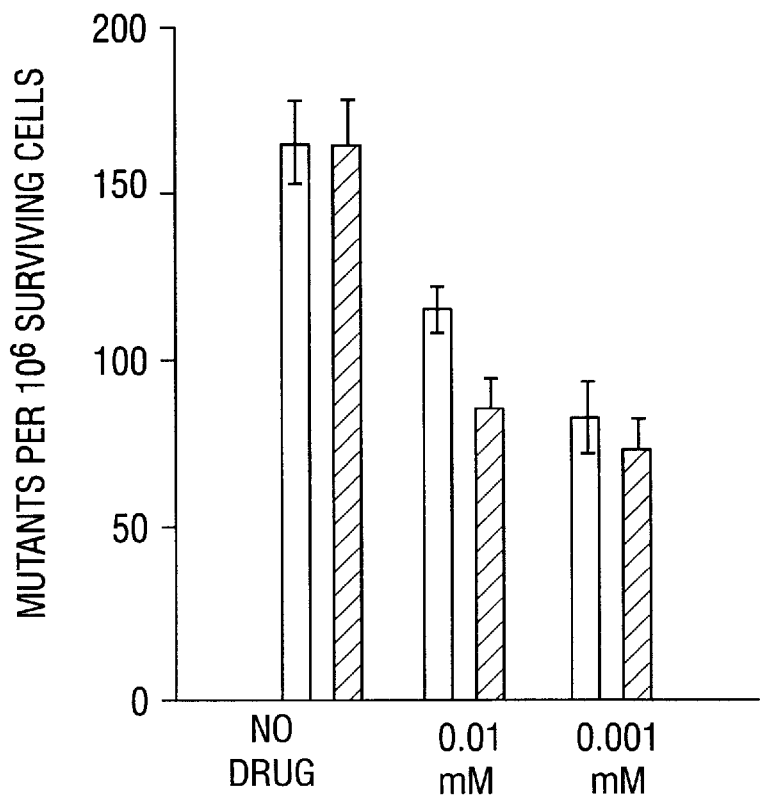
Figure 12I:
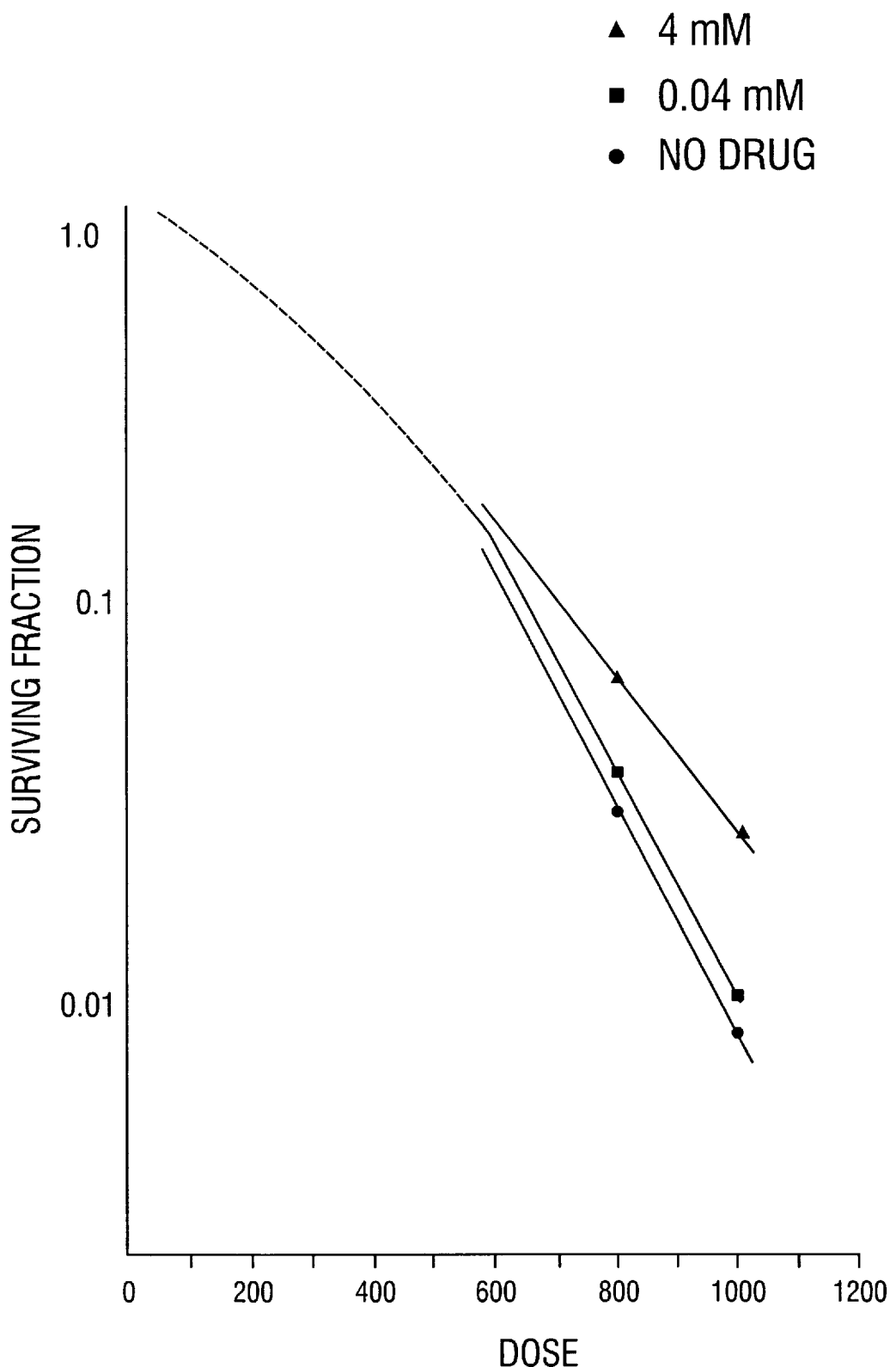
Figure 12J:
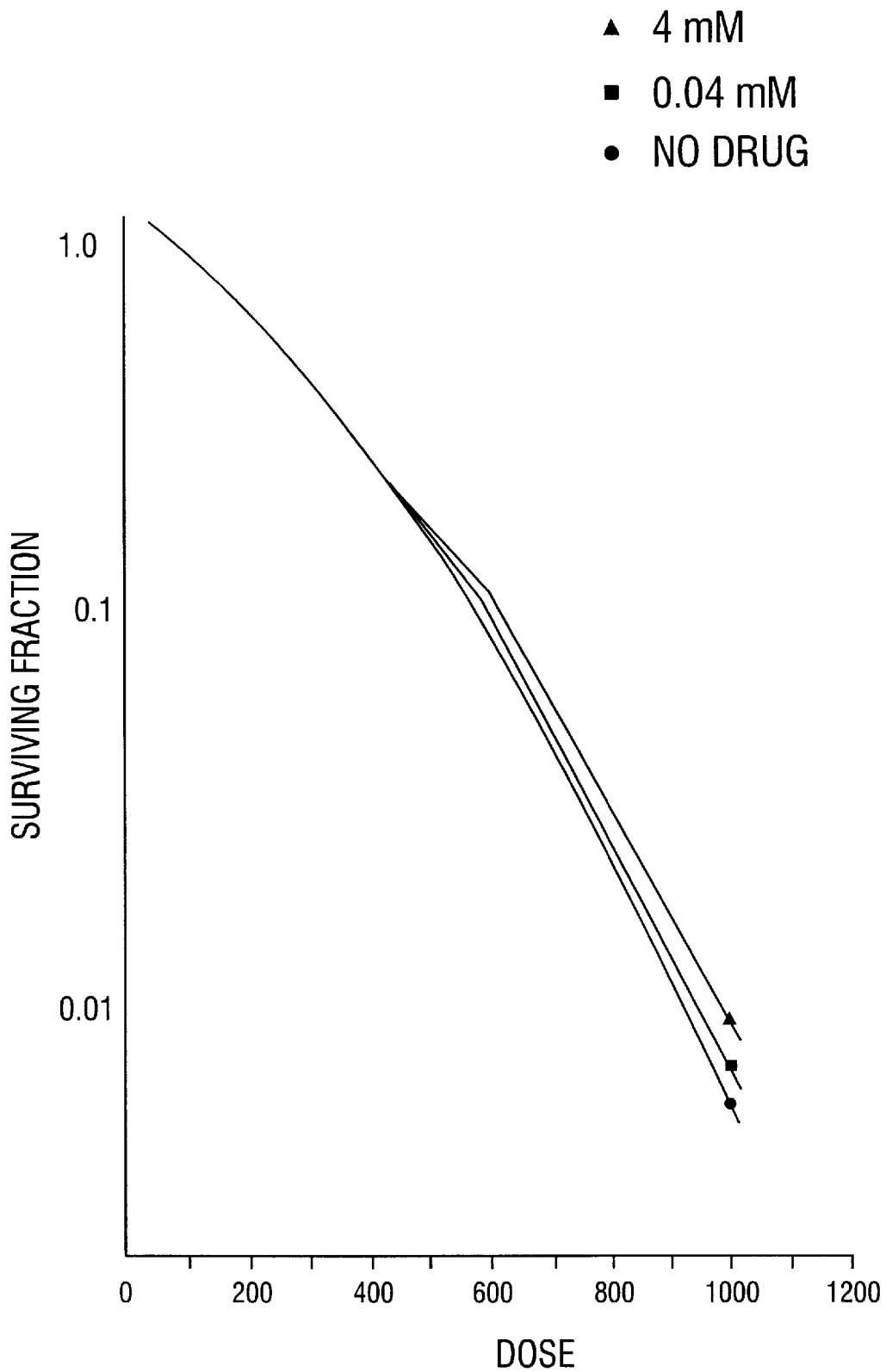
Figure 12K:
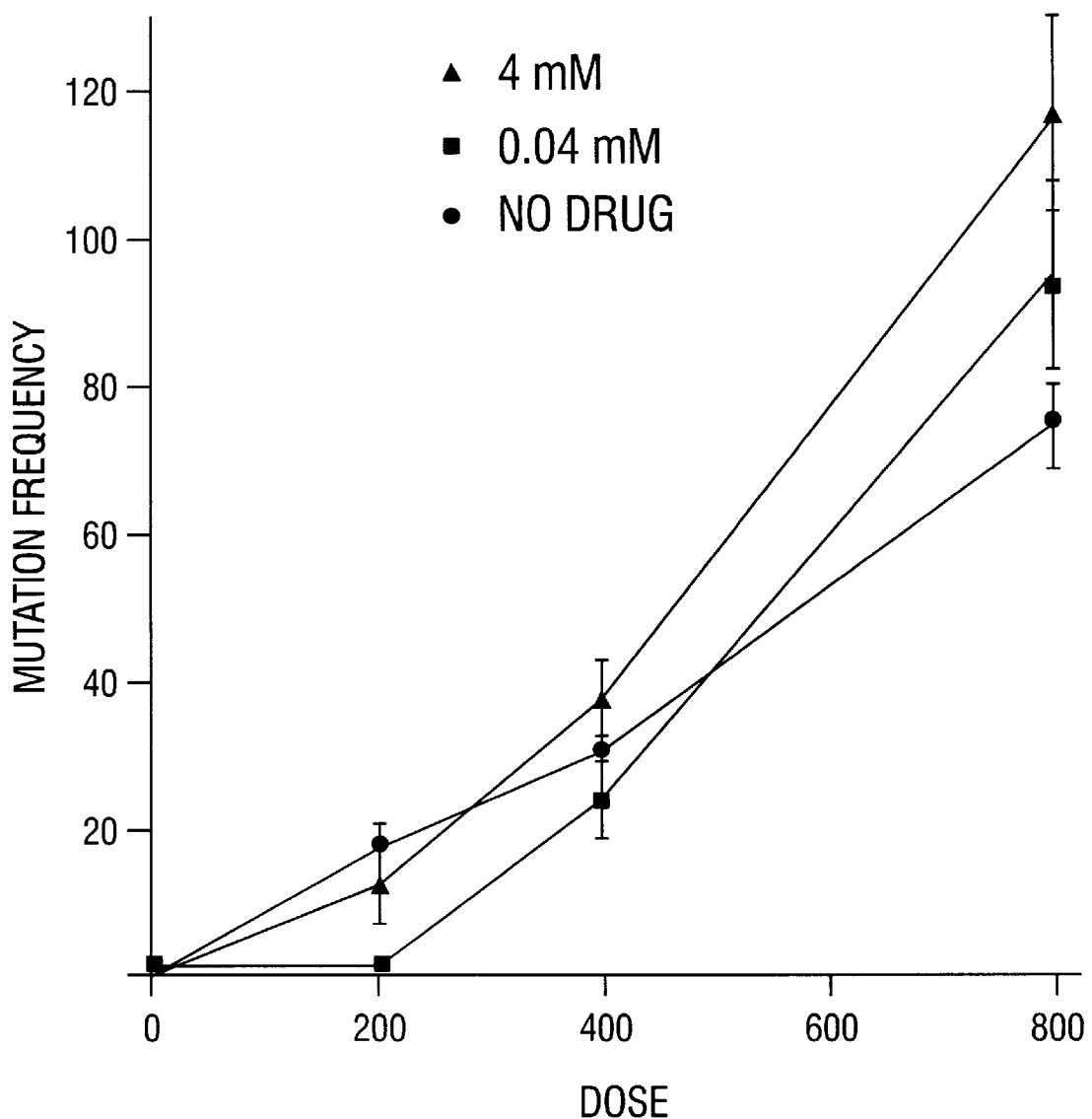

The anti-mutagenic effect of WR-2721 was demonstrated at the hprt locus in mice treated with cytoxan and cisplatin, FIGS. 11C and 11D, respectively. The reduction in mutant frequencies of T-lymphocytes isolated from mice so treated shows WR-2721 and its metabolites to be effective as an antimutagens against chemical as well as radiation insult. The effect of low doses of WR-2721 in the prevention of mutagenesis without affecting the therapeutic effects of cytoxan on tumor cells is further demonstrated as summarized in FIG. 21.

II. Phosphorothioate Protection from Low Dosages.

Figure 2:
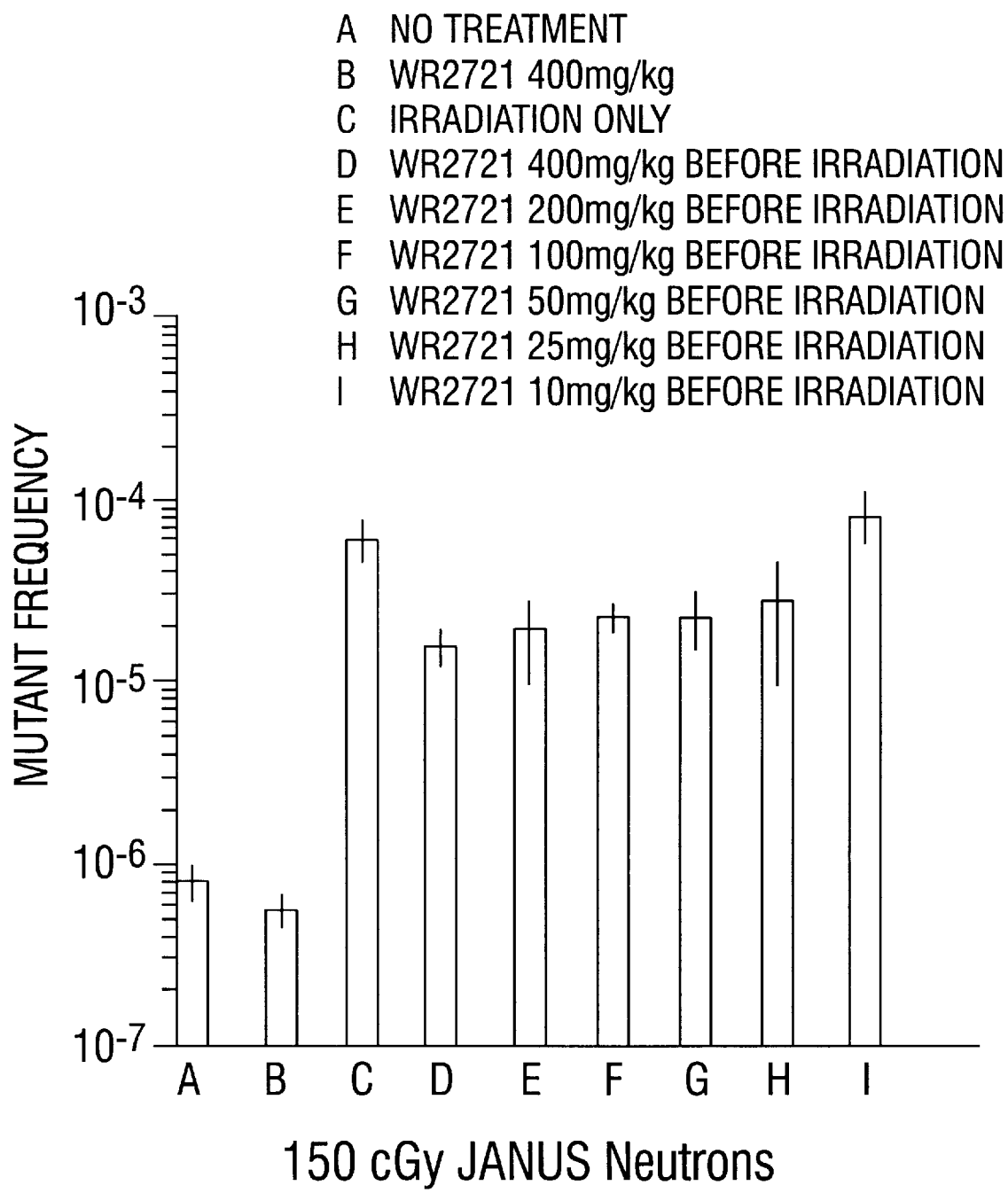
FIG. 2 demonstrates the performance at low concentrations of S-2-(3-aminopropylamino) ethylphosphorothioic acid (i.e., WR-2721) in the range of from 400 mg/kg to 10 mg/kg. Error bars represent one standard error of the mean.
Figure 3:
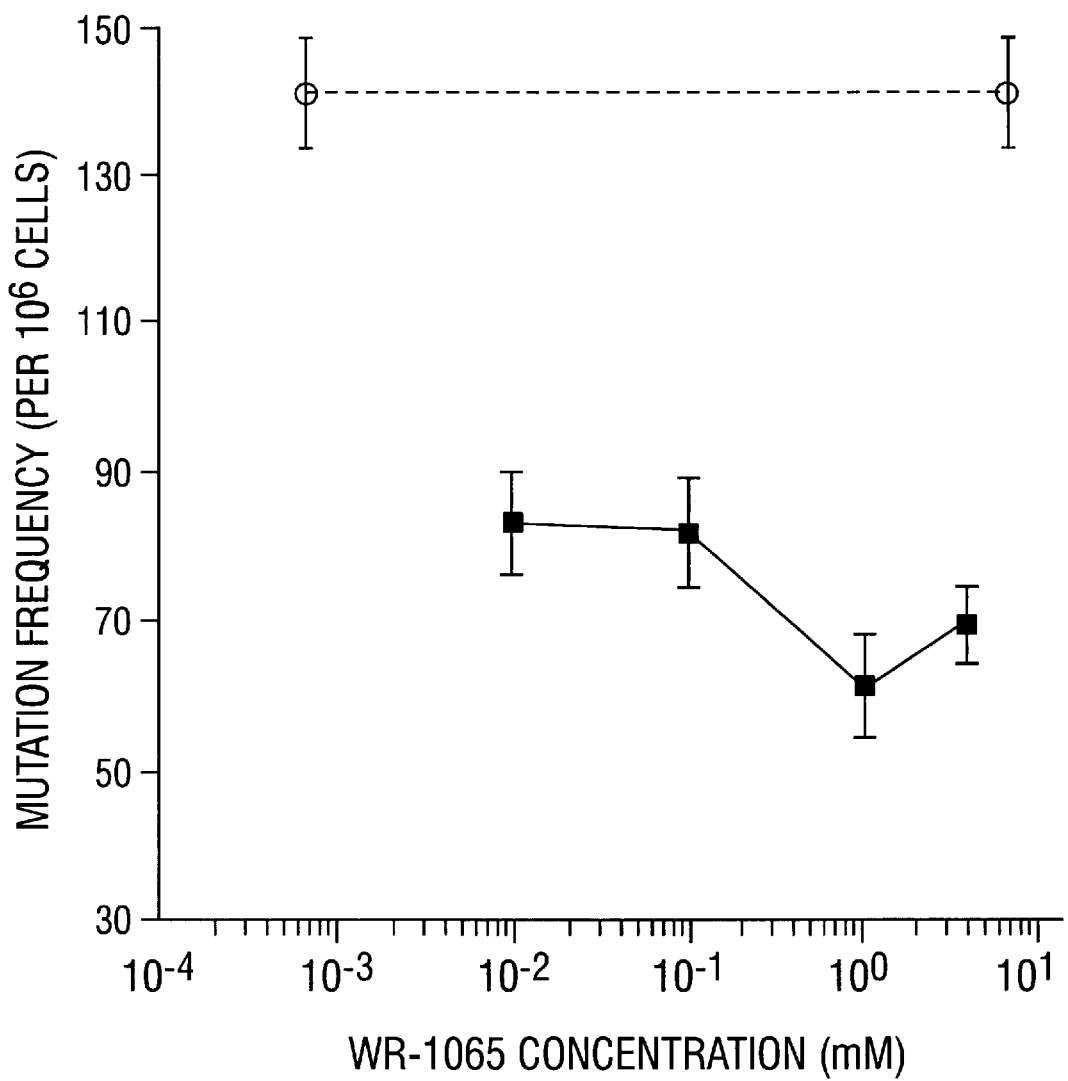
FIG. 3 demonstrates the relationship between the concentration of 2-[(aminopropyl) amino] ethanethiol (i.e., WR-1065) and its protective ability against radiation-induced ($^{60}$Co Gamma-rays, 750 cGy) mutagenesis, using CHO-AA8 cells (irradiated only (○); treated (■). Each error bar is one standard error of the mean.

The phosphorothioates and associated metabolites further achieve mutagen protection at very low concentrations, compared to concentrations required to protect against cell lethality. This conclusion is based on the observations that S-2-(3-aminopropylamino) ethyl phosphorothioic acid is equally antimutagenic at concentrations of 400 mg/kg, 200 mg/kg, 100 mg/kg, and 50 mg/kg (see FIG. 2, ref 10). Mutant frequencies of T lymphocytes isolated from mice irradiated with 150 cGy of fission neutrons were $9.0 \times 10^{-5} \pm 1.2 \times 10^{-5}$ (1 standard error of the mean) for irradiated controls, $1.2 \times 10^{-5} \pm 1.0 \times 10^{-5}$ (S.E.) for 400 mg/kg, $7.8 \times 10^{-6} \pm 2.7 \times 10^{-6}$ (S.E.) for 200 mg/kg, $1.5 \times 10^{-5} \pm 1.4 \times 10^{-6}$ (S.E.) for 100 mg/kg, and $6.3 \times 10^{-6} \pm 3.2 \times 10^{-6}$ (S.E.) for 50 mg/kg. Under in vitro conditions, the free thiol form of S-2-(3-aminopropylamino) ethylphosphorothioic acid, i.e., 2-[(aminopropyl) amino] ethanethiol was administered as an antimutagen to cultured Chinese hamster ovary cells at a concentration range from 4 mM down to 0.1 mM. When administered 30 min prior to irradiation with 750 cGy of $^{60}$Co gamma rays (see FIG. 3), the drug and its metabolite is significantly effective as an antimutagen.

Figure 4:
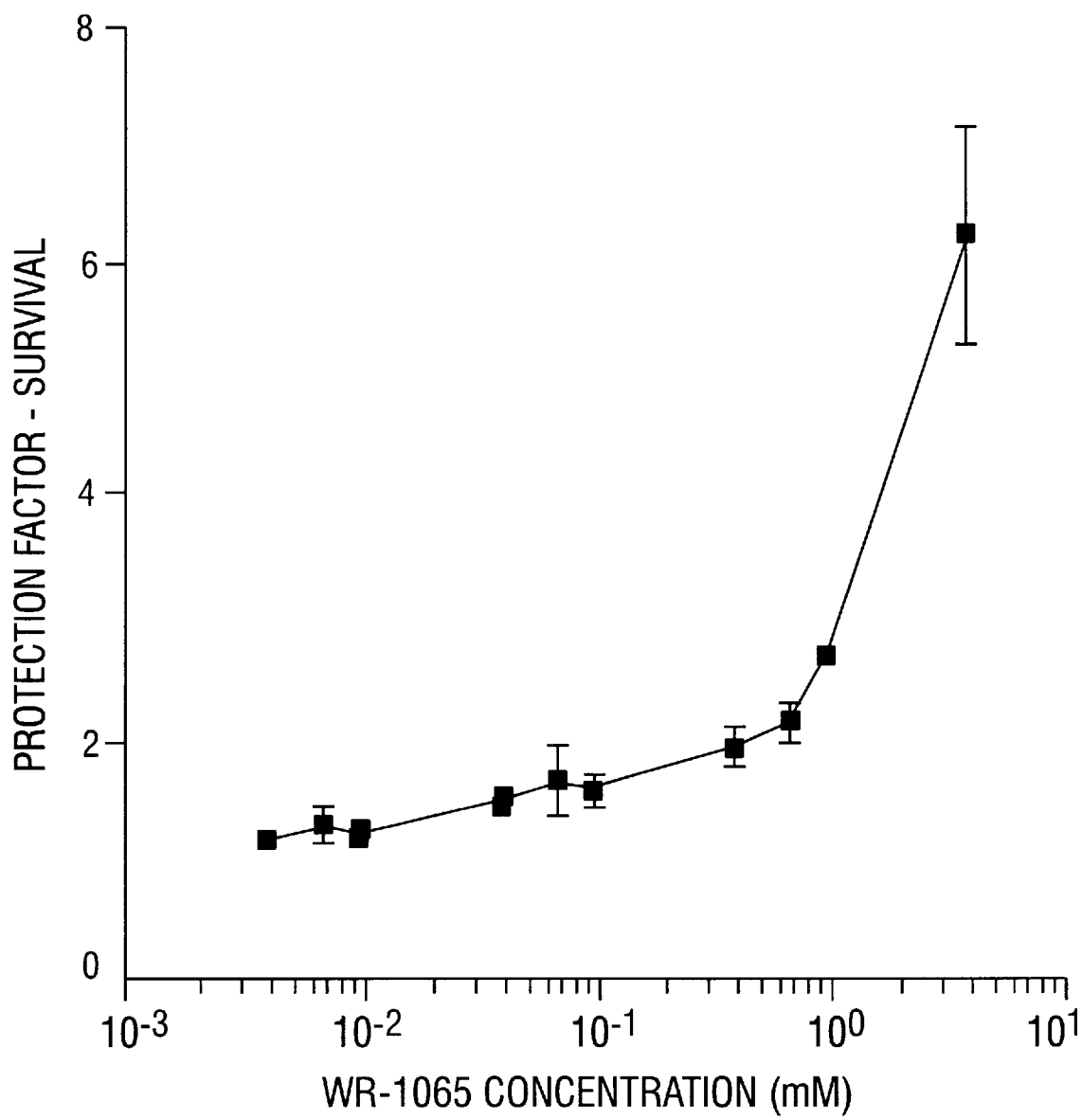
FIG. 4 demonstrates the effect of concentration of 2-[(aminopropyl) amino] ethanethiol (i.e., WR-1065) on its protective ability against radiation-induced ($^{60}$Co Gamma-rays 750 cGy) lethality. Each error bar is one standard error of the mean.

Administration of 2-[(aminopropyl) amino] ethanethiol also results in the formation of its disulfide. Protection against the cell killing effects of radiation by 2-[(aminopropyl) amino] ethanethiol rapidly diminishes as the concentration falls from 4 mM to 0.01 mM (see FIG. 4).

III. Disulfide Metabolite Mutagenic Protection.

Figure 5A:
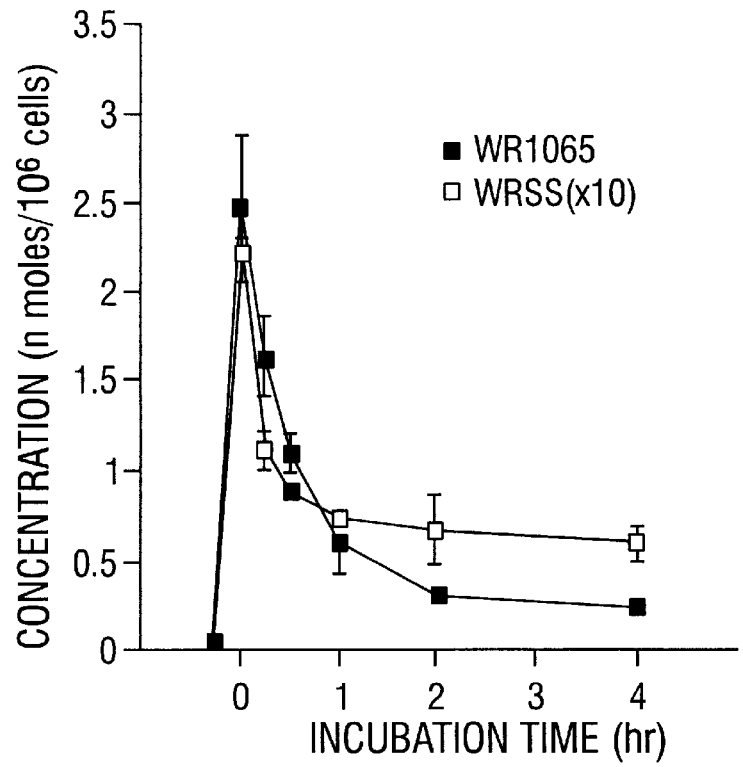
FIG. 5A, FIG. 5B and FIG. 5C.
Figure 5B:
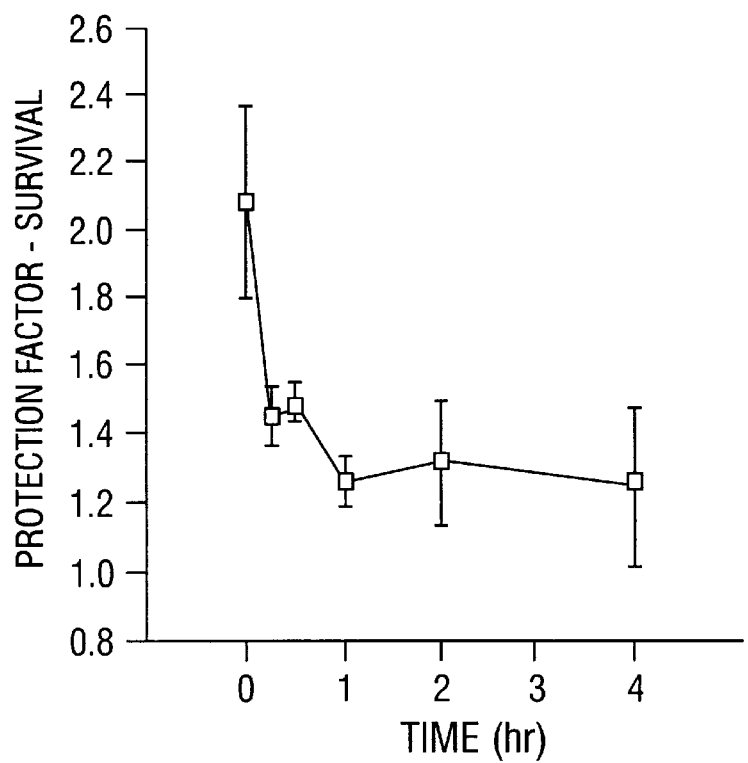
Figure 5C:
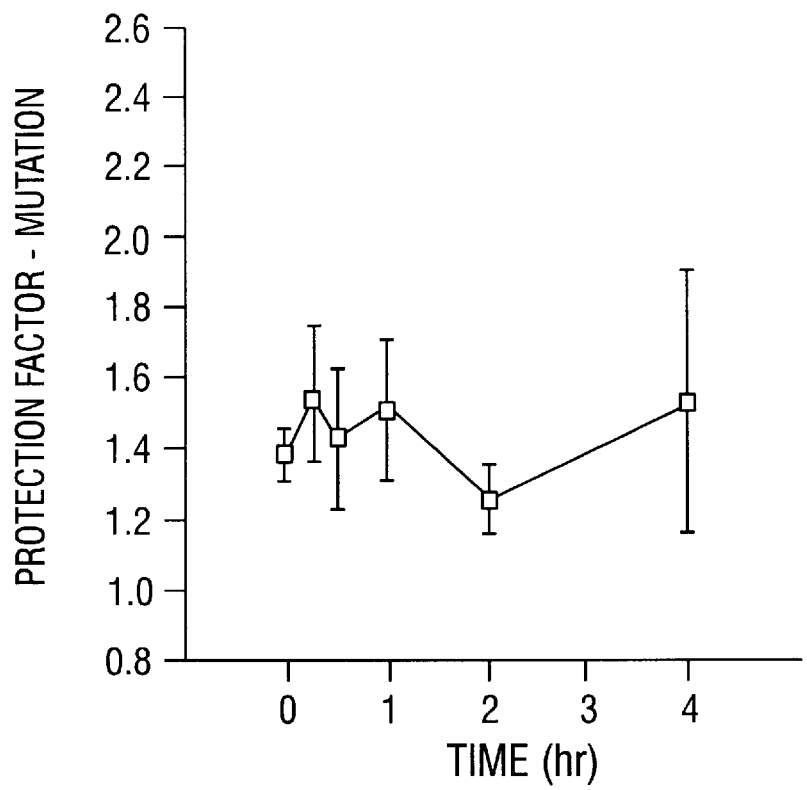

The presence of disulfide metabolite of the phosphorothioate class of compounds corresponds to antimutagenic protection. This conclusion is based on the observations that, following the administration of 4 mM of 2-[(aminopropyl) amino] ethanethiol, protection against radiation-induced (i.e., fission neutrons) somatic mutations at the hypoxanthine-guanine phosphoribosyl transferase locus in Chinese hamster ovary cells correlates with the measured disulfide as compared to the free thiol (see FIG. 5A, FIG. 5B and FIG. 5C).

Figure 6A:
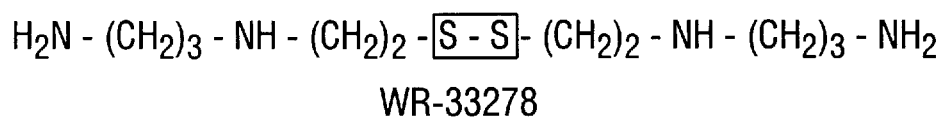
FIG. 6A and FIG. 6B.
Figure 6B:
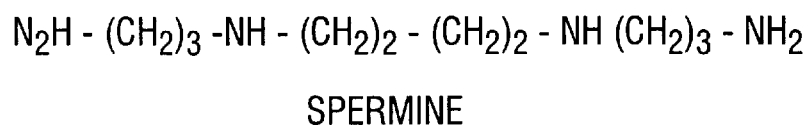
Figures 7G, 7H, 7I, 7J:
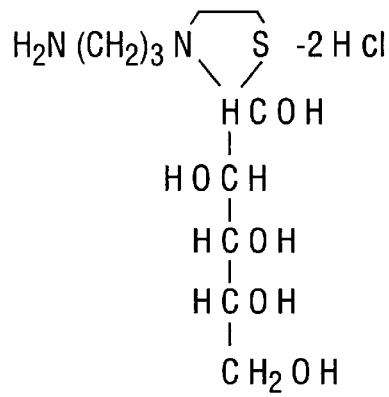

Subsequent thiol and disulfide concentrations were measured by using monobromobiamine (mBBr), which reacts selectively with thiols via a Sn 2 displacement process to produce a fluorescent derivative. These methods were developed to specifically measure 2-[(aminopropyl) amino] ethanethiol, its phosphorothioate, and its disulfide. Chinese hamster ovary cells, $5 \times 10^6$ in 5 ml of growth medium, were administered 4 mM of 2-[(aminopropyl) amino] ethanethiol for 30 min at 37° C. They were then centrifuged, washed with a buffer, and resuspended in fresh medium up to an additional 4 h. After 15 min, 30 min, 1 h, 2 h, and 4 h of incubation, a sample of cells was removed and exposed to 150 cGy of fission neutrons. At these times various measurements made included: survival measurements, mutation measurements, and intracelluar measurements of 2-[(aminopropyl) amino] ethanethiol and its disulfide. The data contained in FIG. 5A, FIG. 5B and FIG. 5C demonstrate that survival protection is well correlated with thiol measurements. This is consistent with conventional understandings and teachings. The disulfide concentration was measured to be significantly less than that of the thiol, but the rate of its decrease with time was less than that found for the thiol. Measured protection against mutagenesis remained constant over this time range correlating with the kinetics of disulfide as opposed to the thiol concentration. The disulfide form of this thiol closely resembles the polyamine spermine (see FIG. 6A and FIG. 6B). Polyamines are known to be involved in the repair of DNA damage due to ionizing and UV irradiation. The measurements indicate an inability to protect against radiation-induced lethality by the phosphorothioate class of chemicals and their associated metabolites when they are added after radiation. Coupling these data with the demonstrated ability to protect against radiation-induced mutagenesis under similar post radiation exposure conditions, make it clear that it is thus the fidelity, not the amount or quantity, of DNA damage which is being affected by these agents. This is also consistent with the properties of polyamines which have been shown to stabilize DNA against enzymatic degradation.

The prior art has indicated that the disulfide is not a protective metabolite of either the phosphorothioates or thiols. The instant data indicates however that the disulfide metabolite of the phosphorothioate is a protective moiety in preventing mutagen- (i.e., radiation) induced somatic mutations. The disulfide metabolite has a close similarity in structure and composition to polyamines, which are known endogenous agents capable of stabilizing chromatin and affecting DNA repair. Further, the phosphorothioates S-2-(3-aminopropylamino) ethyl (WR-2721), S-2-(4-aminobutylamino) ethyl (WR-2822), and S-2-(7-aminoheptylamino) ethyl have been shown in the prior art to competitively inhibit the uptake of the polyamine putrescine into rat lung tissue. The importance of the disulfide moiety in the post mutagen (i.e., radiation) exposure-protection process against the formation of somatic mutations demonstrates a surprising advantage for phosphorothioate compounds which form polyamine-like disulfides for use as antimutagenic chemopreventive agents.

The polyamine spermine and the disulfide WR-33278 are structurally similar agents capable of binding to DNA. As described above, WR-33278 is the disulfide metabolite of the S-2-(3-aminopropylamino)ethylphosphorothioic acid (WR-2721). Because of their reported structural and functional similarties, spermine and WR-33278 were compared with respect to cell survival and mutation induction at the hypoxanthine-guanine phosphoribosyl transferase (hprt) locus in Chinese hamster AA8 cells. Both WR-33278 and spermine were shown to be effective in protecting against radiation-induced mutagenesis, whether administered before or after irradiation.

In order to facilitate both the uptake of WR-33278 into cells and the direct comparison between the protective properties of WR-33278 and spermine, these agents (at concentrations of 0.01 mM and 0.001 mM) were electroporated into cells. Electroporation, 300 V and 125 $\mu$FD, was performed either 30 min prior to or 3 h following exposure of cells to 750 cGy ($^{60}$Co gamma rays) of ionizing radiation. Electroporation alone reduced cell survival to 75% but had no effect on hprt mutation frequency. (FIG. 12A, FIG. 12B, FIG. 12C and FIG. 12D) The electroporation of either spermine or WR-33278 at concentrations greater than 0.01 mM was extremely toxic and, therefore, precluded the study of higher concentrations of these agents. The exposure of cells to both electroporation and irradiation gave rise to enhanced cell killing and mutation induction, with the sequence of irradiation followed 3 h later by electroporation being the more toxic protocol. Cell survival values at a radiation dose of 750 cGy were enhanced by factors of 1.3 and 1.8 following electroporation of 0.01 mM of spermine and WR-33278, respectively, 30 min prior to irradiation. Neither agent was protective at a concentration of 0.001 mM. (See FIG. 12E, FIG. 12F, FIG. 12G and FIG. 12H.)

Protection against radiation-induced hprt mutations was observed for both spermine and WR-33278 under all experimental conditions tested. Spermine at concentrations of 0.01 mM and 0.001 mM administered 30 min before or 3 h after irradiation reduced mutation frequencies by 2.2, 1.2, 1.9 and 2.2, respectively. WR-33278 at concentrations of 0.01 mM and 0.001 mM administered 30 min before or 3 h after irradiation lowered mutation frequencies by factors of 1.8, 1.3, 1.4 and 2.0, respectively.

The close agreement in the magnitudes of effect induced by spermine and WR-33278 against mutagenesis is consistent with their known structural and functional similarities. These data suggest that the properties of radioprotection and chemoprevention exhibited by the phosphorothioate (WR-2721) and associated aminothiol (WR-1065) and disulfide (WR-33278) metabolites may be mediated in part via endogenous polyamine-like processes. Such a mechanism has important implications with respect to the design and development of a new generation drugs for use in radioprotective and chemopreventive agents.

To determine what role, if any, is performed by the amine functionality in either the WR-2721, WR-1065, or WR-33278 anti-mutagens, the radiation survival, protection and anti-mutagenic properties of the aminothiols 1-cysteine and N-acetylcysteine were compared. As shown in FIG. 12I, FIG. 12J and FIG. 12K, 1-cysteine is an effective radioprotector, rendered less effective when the amino group is acetylated (FIG. 12I and FIG. 12J) Protection against radiation-induced mutagenesis at the hpri locus in CHO AA8 cells is also adversely affected, further supporting the proposition that, at least in part, an amine functionality present in conjunction a phosphorothioate, thiol, or disulfide functionality may be responsible for protection against mutagenicity by WR-2721 and its metabolites.

IV. Phosphorothioate Protection Against Mutagenesis

Figure 8:
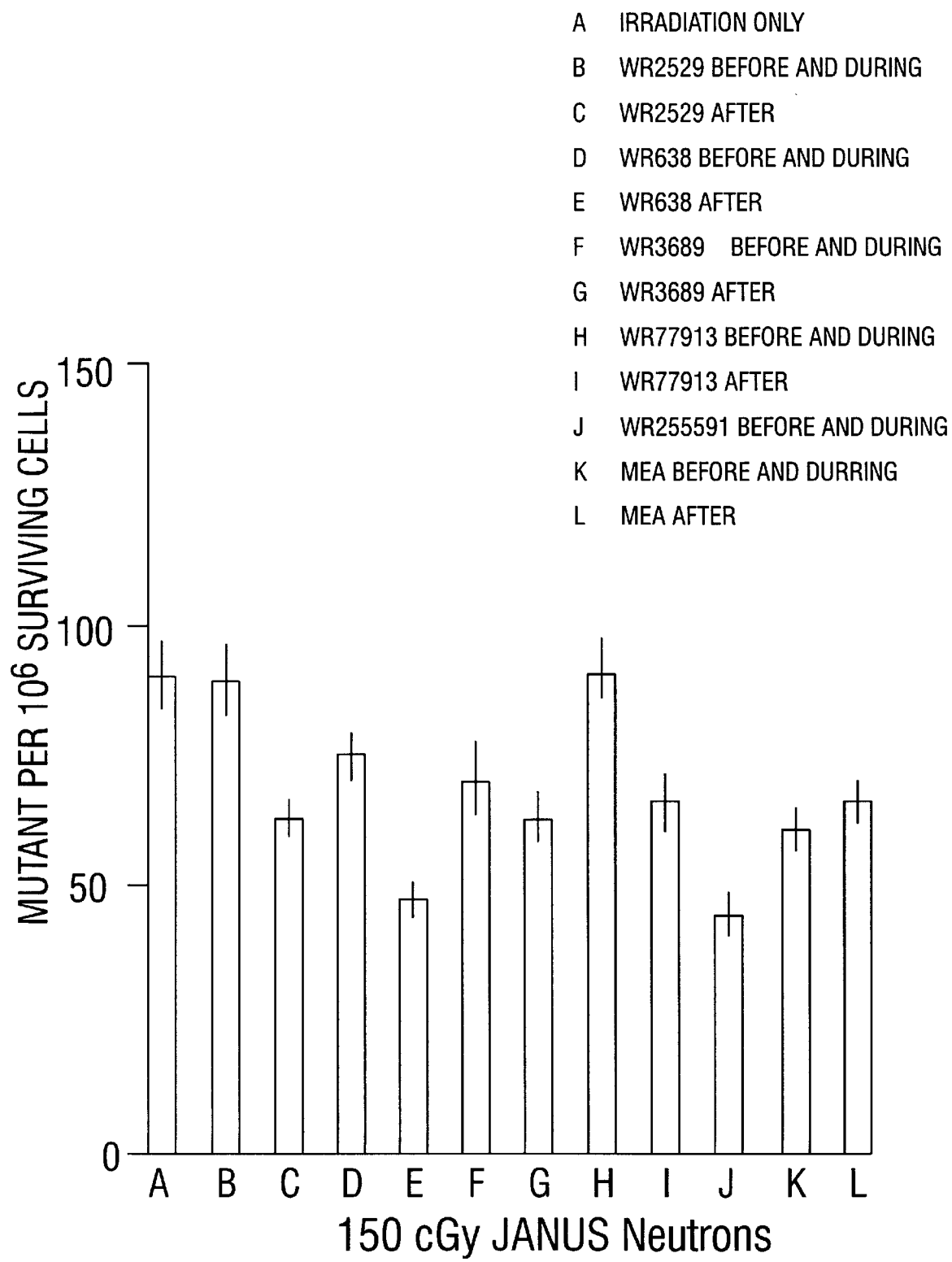
FIG. 8 demonstrates the effectiveness under in vitro conditions of 3-[(2-mercaptoethyl) amino] propionamide p-toluenesulfonate (designated WR-2529); S-1-(aminoethyl) phosphorothioic acid (designated WR-638)

The ability to protect against mutagen-induced somatic mutations is a general property of the phosphorothioates and their associated metabolites. This advantage demonstrated by the data obtained by experiments on cultured Chinese hamster ovary cells first exposed to 150 cGy of fission neutrons and then applying for 30 min a quantity of 4 mM of either 3-[(2-mercaptoethyl)amino] propionamide p-toluenesulfonate (WR-2529), S-1-(aminoethyl) phosphorothioic acid (WR-638), S-[2-(3-methylaminopropyl) aminoethyl]phosphorothioate acid (WR-3689), and S-1-(2-hydroxy-3-amino) propyl phosphorothioic acid (WR-77913) (see FIG. 8). All of these agents, including 2-[3-(methylamino) propylamino]ethanethiol (WR-255591) were effective anti-mutagens when they were added to cells at a concentration of 4 mM at about 30 min prior to exposure to fission neutrons (see FIG. 8).

Figure 9:
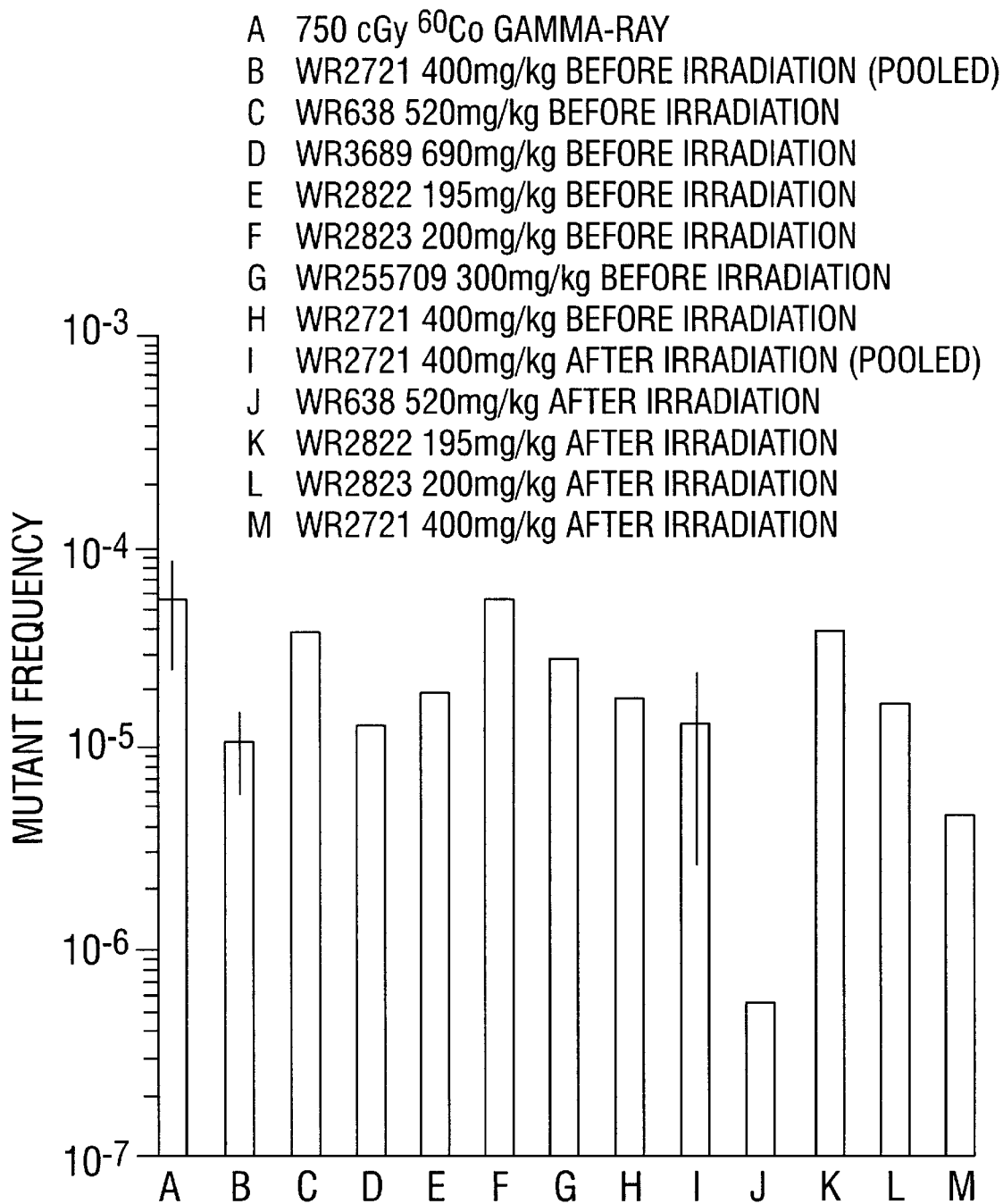
FIG. 9 demonstrates the effectiveness, under in vivo conditions, of S-2-(3-aminopropylamino)ethyl phosphorothioic acid (WR-2721); S-1-(aminoethyl) phosphorothioic acid (WR-638); S-[2-(3-methylaminopropyl) aminoethyl] phosphorothioate acid (WR-3689); S-2-(4-aminobutylamino) ethylphosphorothioic acid (WR-2822); S-2-(5-aminopentylamino) ethyl phosphorothioic aid (WR-2823); 1-[3-(3-aminopropyl) thiazolidin-2-Y1]-D-gluco-1,2,3,4,5-pentane-pentol dihydrochloride (WR-255709), in protecting against radiation-induced mutagenesis as a function of administration either 30 min before or immediately after irradiation of B6CF, mice with 150 cGy of fission-spectrum neutrons.
Figure 10C:
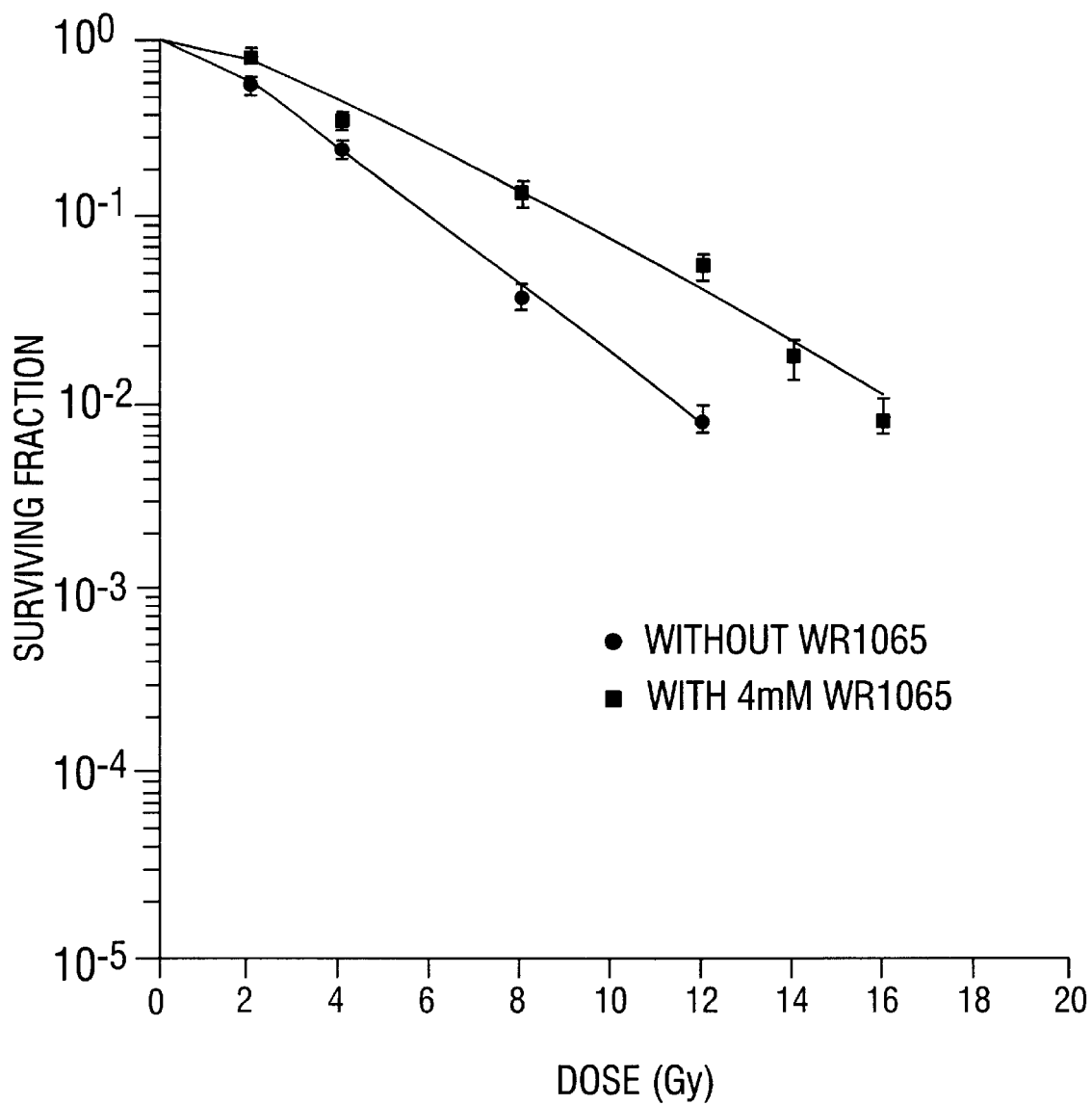
Figure 10D:
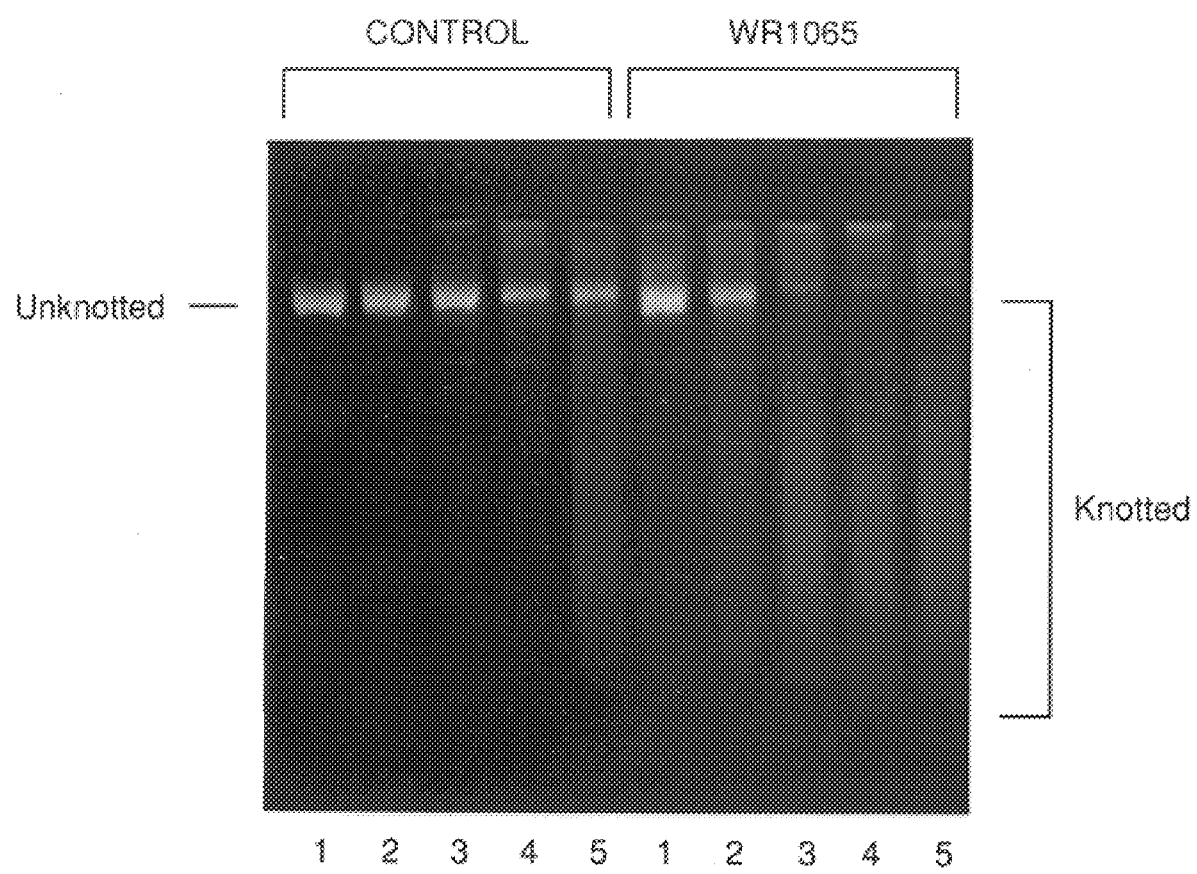
Figure 10E:
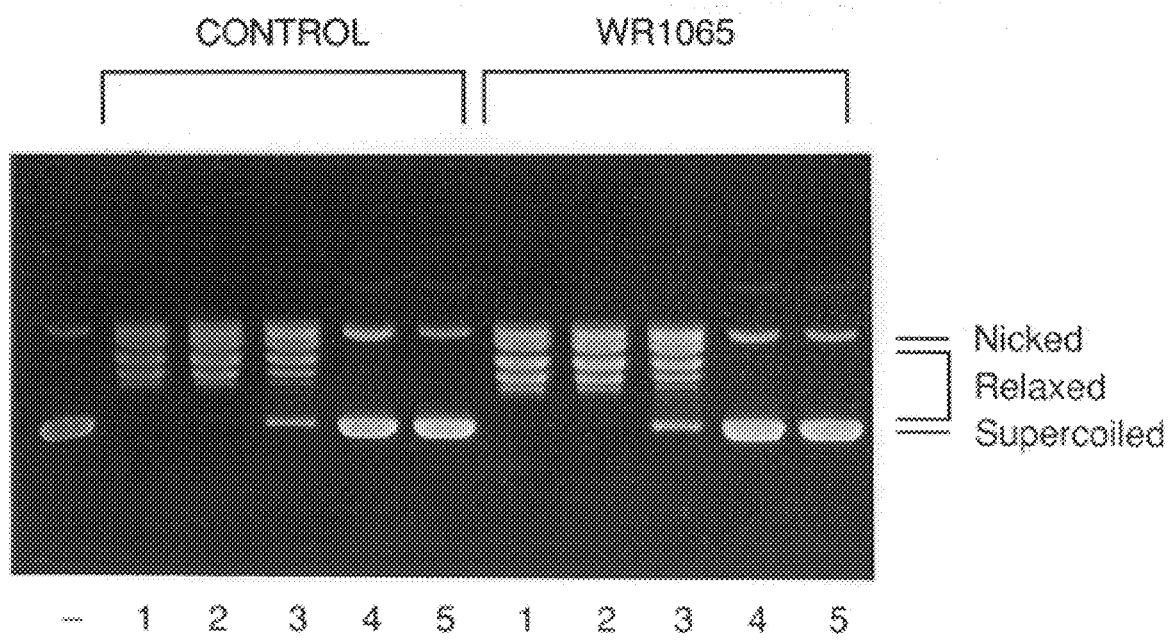
Figure 10F:
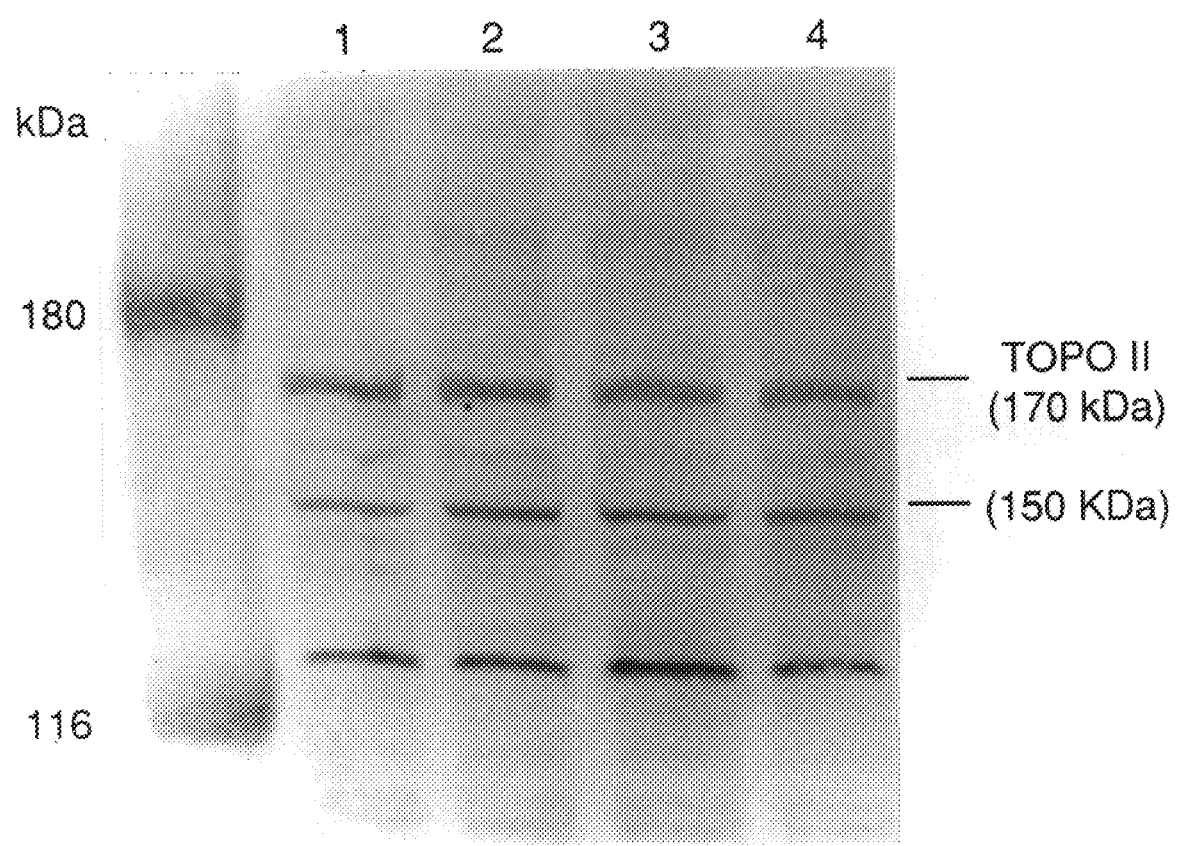
Figure 10G:
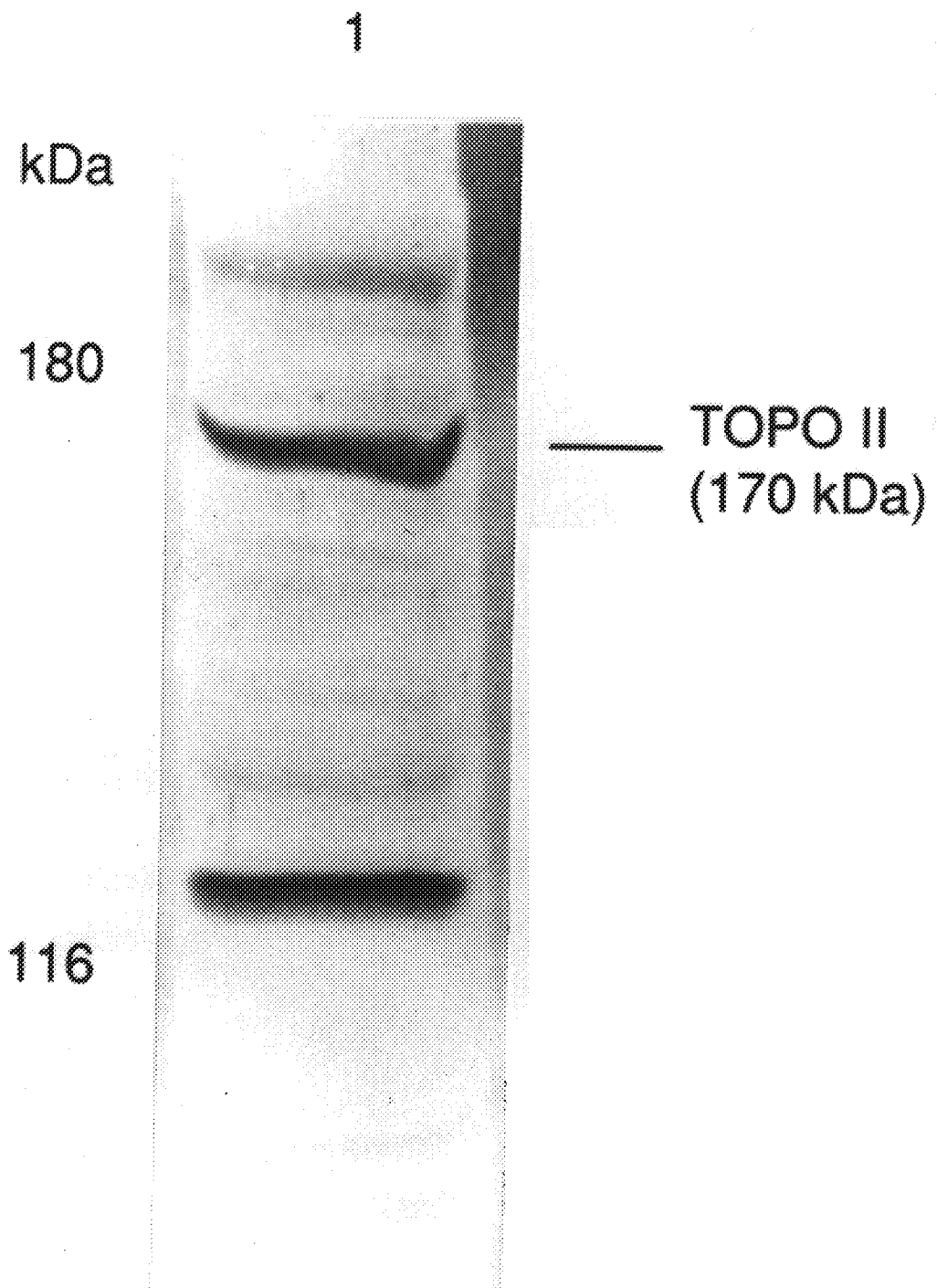
Figures 10H, 10I:
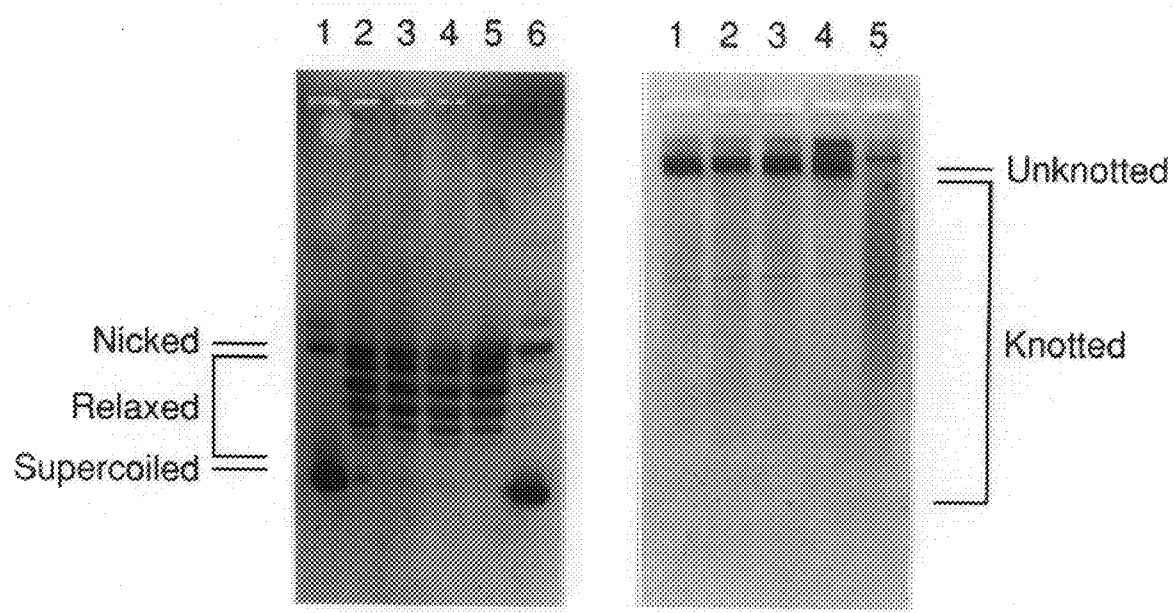
Figure 10J:
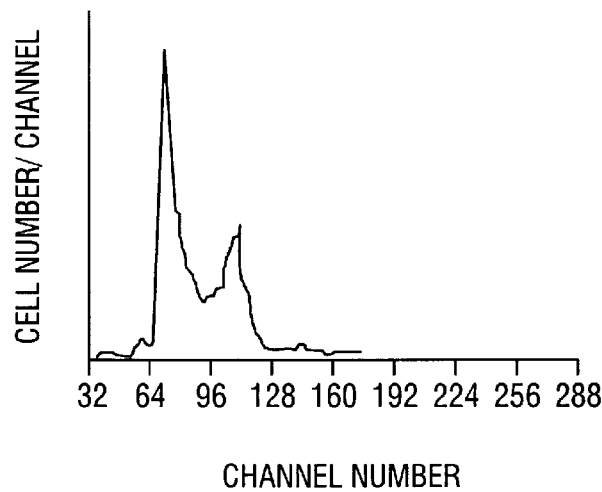
Figure 10K:
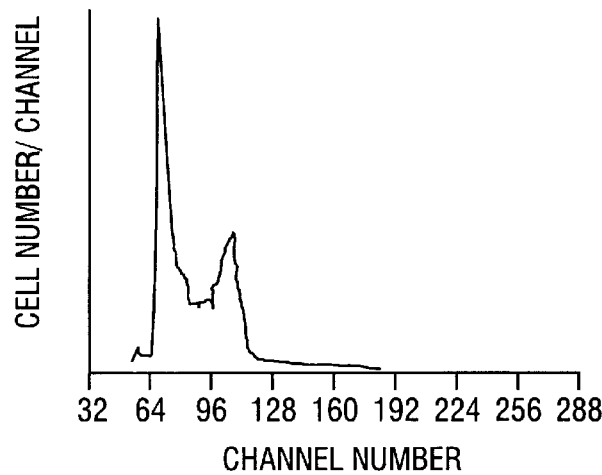
Figure 10L:
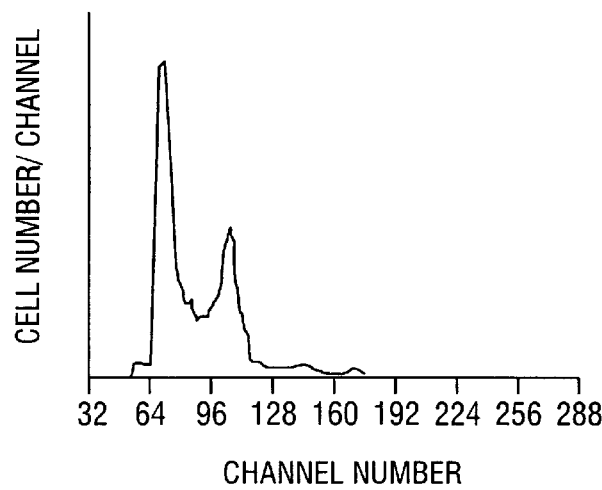
Figure 10M:
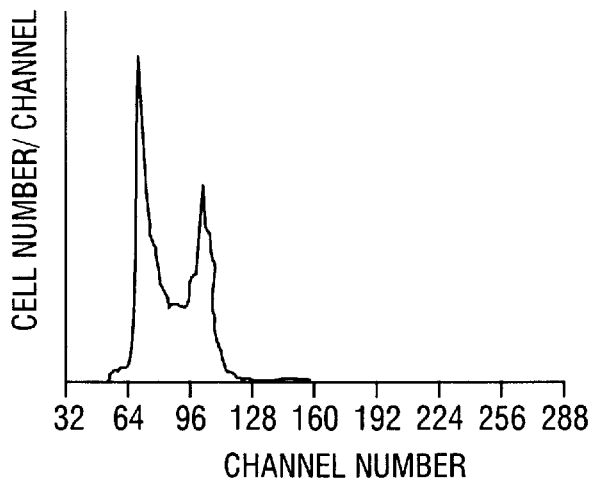
Figure 10N:
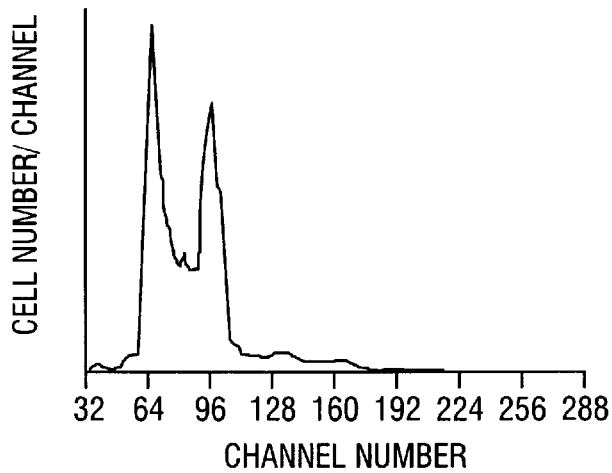
Figure 10O:
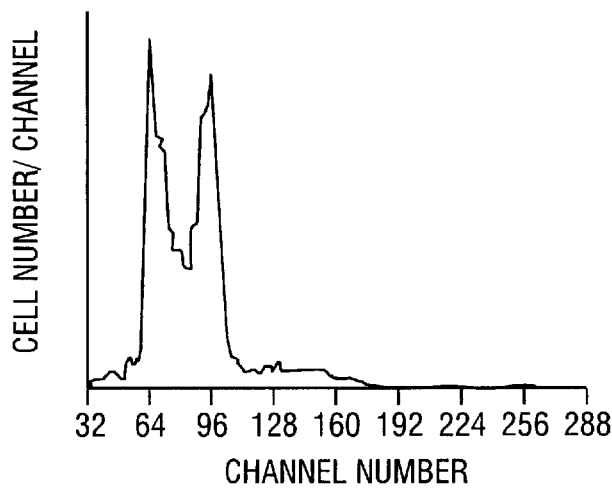
Figure 10P:
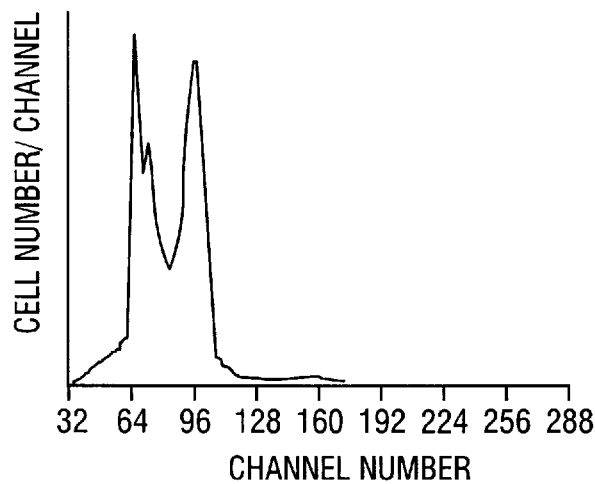
Figure 10Q:
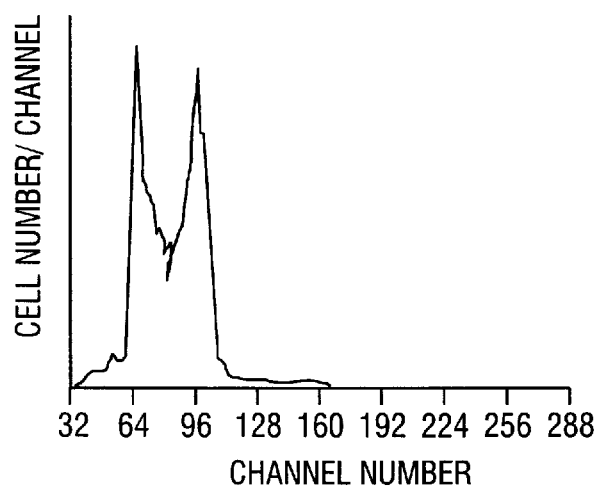

Protection against radiation-induced somatic mutations in mammals (i.e., mice) was also demonstrated for S-1-(aminoethyl) phosphorothioic acid (WR-638) under conditions in which a dose of 520 mg/kg was administered ip to animals within about 10 min after whole-body exposure to 750 cGy of $^{60}$Co gamma rays (see FIG. 9). Phosphorothioates exhibited antimutagenic properties in mammals when administered 30 min prior to exposure to 750 cGy of $^{60}$Co gamma rays. The phosphorothioates included S-[2-(3-methylaminopropyl) aminoethyl] phosphorothioate acid (WR-3689), and S-2-(4-aminobutylamino) ethylphosphorothioic acid (WR-2822). These data demonstrate that the antimutagenic properties of S-2-(3-aminopropylamino) ethylphosphorothioic acid (WR-2721) are also observable in selected ones of the phosphorothioates and their associated metabolites.

While preferred embodiments of the invention have been shown and described, it will be clear to those skilled in the art that various changes and modifications can be made without departing from the invention in its broader aspects as set forth in the claims provided hereinafter.

What is claimed is:

1. A method for altering gene expression in mammalian cells, comprising contacting mammalian cells with a chemical compound selected from the group consisting of an aminoalkylphosphorothioate and an associated aminoalkylphosphorothioate metabolite in an amount effective to modulate gene expression in said mammalian cells.

2. The method of claim 1 wherein said amount is equivalent to about 40 $\mu$M.

3. The method of claim 1 wherein said compound is S-1-(aminoethyl) phosphorothioic acid (WR-638).

4. The method of claim 1 wherein said compound is S-[2-(3-methylaminopropyl)aminoethyl]phosphorothioate (WR-3689).

5. The method of claim 2 wherein said compound is S-2-(4-aminobutylamino) ethylphosphorothioic acid (WR-2822).

6. The method of claim 1 wherein said compound is S-1-(2-hydroxy-3-amino)propyl phosphorothioic acid (WR-77913).

7. The method of claim 1 wherein said compound is S-2-(5-aminopentylamino) ethyl phosphorothioic acid (WR-2823).

8. The method of claim 1 wherein said compound is 1-[3-(3-aminopropyl) thiazolidin-2-yl]-D-gluco-1,2,3,4,5 pentane-pentol dihydrochloride (WR255709).

9. The method of claim 1 wherein said compound is S-2-[3-(aminopropyl)amino]ethylphosphorothioic acid (WR-2721).

10. The method of claim 1 wherein said compound is 2-[(aminopropyl)amino]ethanethiol (WR-1065).

11. The method of claim 1 wherein said compound is [2-[(aminopropyl)amino]ethanethiol]N,N,'-dithiodi-2,1-(ethanediyl)bis-1,3-propanediamine (WR-33278).

12. The method of claim 1 wherein lamin gene expression is altered.

13. The method of claim 1 wherein thymidine kinase gene expression is altered.

14. The method of claim 1 wherein protein kinase gene expression is altered.

15. The method of claim 1 wherein said chemical compound is an aminoalkylphosphorothioate which forms a polyamine disulfide under conditions of cellular metabolism.

16. The method of claim 1 wherein said compound is 2-[3-(methylamino)propylamino] ethanethiol (WR-255591).

17. The method of claim 1, wherein said mammalian cells are located in a mammal and said compound is administered to said mammal.

18. The method of claim 17, wherein the amount of said compound administered is about 400 mg/kg.

19. The method of claim 18, wherein the amount of said compound administered is about 50 mg/kg.

20. The method of claim 19, wherein the amount of said compound administered is about 25 mg/kg.

21. The method of claim 17, wherein said mammal is irradiated.

22. The method of claim 21, wherein said mammal is irradiated at a time from about 30 minutes prior to administration of said compound up to about three hours after administration of said compound.

23. The method of claim 22 wherein said compound is administered about 30 minutes before irradiation of the mammal.

24. A method for altering gene expression in mammalian cells, comprising:

(a) contacting mammalian cells with a chemical compound selected from the group consisting of an aminoalkylphosphorothioate and an associated aminoalkylphosphorothioate metabolite, in an amount effective to modulate gene expression in said mammalian cells; and (b) confirming the alteration of gene expression in said mammalian cells.

25. The method of claim 24, wherein said compound is S-1-(aminoethyl) phosphorothioic acid (WR-638).

26. The method of claim 24 wherein said compound is S-[2-(3-methylaminopropyl)aminoethyl]phosphorothioate (WR-3689).

27. The method of claim 24 wherein said compound is S-2-(4-aminobutylamino) ethylphosphorothioic acid (WR-2822).

28. The method of claim 24 wherein said compound is S-1-(2-hydroxy-3-amino)propyl phosphorothioic acid (WR-77913).

29. The method of claim 24 wherein said compound is S-2-(5-aminopentylamino)ethyl phosphorotioic acid (WR-2823).

30. The method of claim 24 wherein said compound is 1-[3-(3-aminopropyl)thiazolidin-2-yl]-D-gluco-1,2,3,4,5 pentane-pentol dihydrochloride (WR255709).

31. The method of claim 24 wherein said compound is S-2-[3-(aminopropyl)amino]ethylphosphorothioic acid (WR-2721).

32. The method of claim 24 wherein said compound is 2-[(aminopropyl)amino]ethanethiol (WR-1065).

33. The method of claim 24 wherein said compound is [2-[(aminopropyl)amino]ethanethiol] N,N,'-dithiodi-2,1-(ethanediyl)bis-1,3-propanediamine (WR-33278).

34. The method of claim 24 wherein said compound is 2-[3-(methylamino)propylamino] ethanethiol (WR-255591).

35. The method of claim 24 wherein said chemical compound is an aminoallylphosphorothioate that forms a polyamine disulfide under conditions of cellular metabolism.

36. The method of claim 24 wherein lamin gene expression is altered.

37. The method of claim 24 wherein thymidine kinase gene expression is altered.

38. The method of claim 24 wherein protein kinase gene expression is altered.

39. The method of claim 24, wherein said mammalian cells are located in a mammal and said compound is administered to said mammal.

40. The method of claim 39, wherein the amount of said compound administered is about 400 mg/kg.

41. The method of claim 40, wherein the amount of said compound administered is about 50 mg/kg.

42. The method of claim 41, wherein the amount of said compound administered is about 25 mg/kg.

43. The method of claim 39, wherein said mammal is irradiated.

44. The method of claim 43 wherein said mammal is irradiated at a time from about 30 minutes prior to administration of said compound up to about three hours after administration of said compound.

45. The method of claim 44 wherein said compound is administered about 30 minutes before irradiation of the mammal.

* * * * *

UNITED STATES PATENT AND TRADEMARK OFFICE
CERTIFICATE OF CORRECTION

PATENT NO. : 5,869,338
DATED : February 9, 1999
INVENTOR(S) : Grdina

It is certified that error appears in the above-identified patent and that said Letters Patent is hereby corrected as shown below:

In claim 5, cloumn 18, line 28, delete "2", and insert the following therefor: -- 1 --.

In claim 35, delete "aminoallylphosphorothioate", and insert the following therefor: -- aminoalkylphosphorothioate --.

Signed and Sealed this

Twentieth Day of July, 1999

Attest:

Q. TODD DICKINSON

*Attesting Officer*  *Acting Commissioner of Patents and Trademarks*